United States Patent
Wu et al.

(10) Patent No.: US 9,809,560 B2
(45) Date of Patent: Nov. 7, 2017

(54) LIGANDS AND METHODS FOR LABELING BIOMOLECULES IN VIVO

(75) Inventors: Peng Wu, New Rochelle, NY (US); David Soriano del Amo, Bronx, NY (US); Wei Wang, Port Jefferson Station, NY (US); Florence L. Marlow, New Rochelle, NY (US)

(73) Assignee: Albert Einstein College of Medicine, Inc., Bronx, NY (US)

( * ) Notice: Subject to any disclaimer, the term of this patent is extended or adjusted under 35 U.S.C. 154(b) by 612 days.

(21) Appl. No.: 13/813,163

(22) PCT Filed: Aug. 5, 2011

(86) PCT No.: PCT/US2011/046700
§ 371 (c)(1),
(2), (4) Date: Jul. 25, 2013

(87) PCT Pub. No.: WO2012/021390
PCT Pub. Date: Feb. 16, 2012

(65) Prior Publication Data
US 2013/0295019 A1    Nov. 7, 2013

Related U.S. Application Data

(60) Provisional application No. 61/401,189, filed on Aug. 9, 2010.

(51) Int. Cl.
C07D 249/00    (2006.01)
C07D 249/04    (2006.01)
G01N 33/533    (2006.01)
G01N 33/58     (2006.01)
A61K 49/00     (2006.01)

(52) U.S. Cl.
CPC ........ *C07D 249/04* (2013.01); *A61K 49/0052* (2013.01); *G01N 33/533* (2013.01); *G01N 33/582* (2013.01)

(58) Field of Classification Search
CPC combination set(s) only.
See application file for complete search history.

(56) References Cited

U.S. PATENT DOCUMENTS

2008/0241856 A1    10/2008    Wong et al.
2010/0197871 A1     8/2010    Finn et al.

OTHER PUBLICATIONS

Jlalia et al. Molecules 2010, 15, 3087-3120.*
Wang W et al., entitled "Sulfated Ligands for the Copper(I)-Catalyzed Azide-Alkyne Cycloaddition," Chem. Asian J., 2011, 6, 2796-2802.
PCT International Search Report dated Dec. 27, 2011 in connection with PCT International Patent Application No. PCT/US2011/46700, 5 pages.
PCT Written Opinion of the International Searching Authority dated Dec. 27, 2011 in connection with PCT International Patent Application No. PCT/US2011/46700, 6 pages.
Hein J E et al., entitletd "Copper-catalyzed azide-alkyne cycloaddition (CuAAC) and beyond: new reactivity of copper (I) acetylides," Chem Soc Rev. Apr. 2010; 39(4):1302-1315.
De Munno G et al., entitled "Magneto-Structural Effects of the Jahn-Teller Distortions on 2,2'-Bipyrimidine- (bpm-) Bridged Dinuclear Copper(II) Complexes: Crystal Structures and Magnetic Properties of [Cu2(bpm)(H2O)4(SO4) 2]-3H2O and [Cu2(bpm)(H2O)8](SO4)2-H2O," Inorg. Chem. 1995, 34, 2048-2053.
Meldal M et al., entitled "Cu-Catalyzed Azide-Alkyne Cycloaddition," Chem. Rev. 2008, 108, 2952-3015.

* cited by examiner

*Primary Examiner* — Robert Cabral
(74) *Attorney, Agent, or Firm* — Amster, Rothstein & Ebenstein LLP

(57) ABSTRACT

Disclosed are tris(triazolylmethyl)amine ligands, and kits and methods for labeling and/or imaging a biomolecule of interest in a subject or living system.

9 Claims, 17 Drawing Sheets

A

B

LIGANDS AND METHODS FOR LABELING BIOMOLECULES IN VIVO

CROSS-REFERENCE TO RELATED APPLICATIONS

This application is a U.S. national stage entry under 35 U.S.C. §371 of PCT International Patent Application No. PCT/US2011/046700, filed Aug. 5, 2011, which claims priority to U.S. Provisional Patent Application No. 61/401,189, filed Aug. 9, 2010, the contents of which are incorporated herein by reference in their entirety.

STATEMENT OF GOVERNMENT SUPPORT

This invention was made with government support under grant number GM080585 awarded by the National Institutes of Health. The government has certain rights in the invention.

FIELD OF THE INVENTION

The present invention relates generally to ligands and methods for labeling and/or imaging biomolecules in vivo.

BACKGROUND OF THE INVENTION

Throughout this application various publications are referred to in brackets. Full citations for these references may be found at the end of the specification. The disclosures of these publications are hereby incorporated by reference in their entirety into the subject application to more fully describe the art to which the subject invention pertains.

The recent development of bioorthogonal click chemistry has led to an explosion of interest in selective covalent labeling of biomolecules in cells and living organisms [1, 2]. In these labeling reactions one of the two bioorthogonal functional groups is first incorporated into target biomolecules via genetic [3] or metabolic approaches [4, 5]. A biophysical probe, functionalized in a complementary fashion, is introduced in a second step, allowing detection or isolation of the target of interest. To minimize perturbations to the physiological state of the cells or organisms probed, an ideal ligation reaction must proceed with water at neutral pH and at temperatures between 25 to 37° C. without any cytotoxic effects. Further, the reactive partners participating in this transformation must be inert to the native functional groups present in the biological system [6, 7].

Few chemical reactions satisfy both the bioorthogonal and click requirements. Discovered by Sharpless-Fokin/Meldal in 2002, the Cu(I)-catalyzed azide alkyne cycloaddition (CuAAC) is the quintessential bioorthogonal click reaction for chemical biologists (FIG. 1A) [8, 9]. This transformation is accelerated by approximately seven orders of magnitude compared to the uncatalyzed version [10]. As a ligand-assisted process, the reaction is further accelerated by Cu(I)-stabilizing ligands (i.e. tris[(1-benzyl-1H-1,2,3-triazol-4-yl)methyl]amine, TBTA, (FIG. 1B, 1C) [11]. The fast reaction kinetics and exquisite selectivity of CuAAC has gained it widespread utilization in chemical biology and materials science [12, 13].

To date, however, the use of CuAAC in living systems has been hampered by the toxicity associated with the catalyst formulations (CuSO$_4$ or CuBr+sodium ascorbate+TBTA) [7]. TBTA, the ligand utilized in the optimized CuAAC conditions to stabilize the Cu(I) oxidation state, has very poor water solubility, which mandates the use of high Cu loading (0.2-1 mM) to achieve reasonable reaction rates. Free Cu(I) ions that escape from the coordination sphere of TBTA promote the generation of reactive oxygen and nitrogen species and induce detrimental consequences to cellular metabolism [14]. For example, *Escherichia coli* that incorporated azidohomoalanine into their outer membrane protein OmpC survived the initial treatment with 100 µM CuBr for 16 h, but were no longer able to divide [15]. Similarly, greater than 90% of mammalian cells underwent apoptosis and cell lysis within 20 min when treated with 1 mM Cu(I) under optimized CuAAC conditions. Zebrafish embryos exhibited a similar sensitivity to Cu(I). When embryos were treated with 1 mM CuSO$_4$, 1.5 mM sodium ascorbate, and 0.1 mM TBTA ligand, all the embryos were dead within 15 min [7]. As presently formulated, labeling of biomolecules via CuAAC is not feasible in living systems.

To improve upon the biocompatibility of the azide-alkyne cycloaddition, Bertozzi and coworkers have developed a copper-free [3+2] cycloaddition by employing ring strains as an alternative means for alkyne activation [16, 17]. Among the cycloalkynes examined, a difluorinated cyclooctyne, DIFO [18], and a biarylazacyclooctynone, BARAC [19], showed rapid kinetics in biomolecular labeling experiments. DIFO-fluorophore conjugates are particularly sensitive for imaging azide-tagged glycans within complex biological systems, including live cells [18], *C. elegans* [20] and zebrafish embryos [21], with very low background fluorescence. However, recent in vivo studies revealed that DIFO-based probes bind to mouse serum albumin non-specifically [22]. In addition, the construction of these cyclooctyne-based probes usually involves multistep linear synthesis, which can be a challenge [18, 23]. A major goal in this field is to identify a new copper catalyst formulation that can promote rapid azide-alkyne cycloaddition in living systems without cytotoxicity.

The present invention addresses this need by providing a ligand that renders the CuAAC biocompatible and extends the application of CuAAC to label biomolecules in living systems. Therefore, the ligand of the present invention allows for the in vivo imaging or profiling of biomolecules. Additionally, the ligand of the present invention allows for the diagnosis and treatment of diseases.

SUMMARY OF THE INVENTION

The present invention provides a Cu(I)-stabilizing ligand for use in azide-alkyne cycloaddition reactions in a living system or subject wherein the ligand comprises a tris(triazolylmethyl)amine of formula (I):

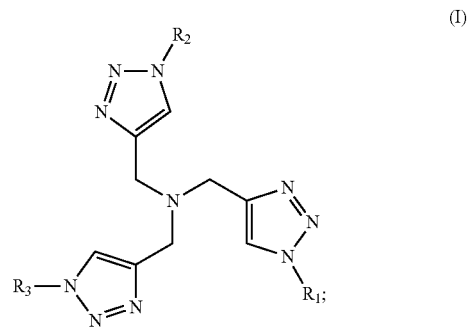

wherein R1 and R2 are independently

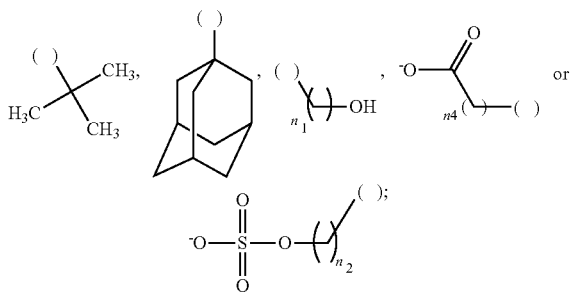

wherein R3 is

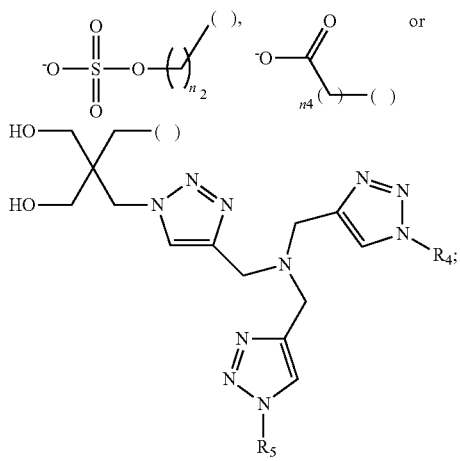

wherein R4 and R5 are independently

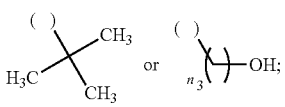

wherein n1, n2 and n3 are independently 2-3, and n4 is 1-2; and wherein ( ) is the point of attachment of the R1, R2, R3, R4 or R5 group to the ring structure.

The present invention also provides a method of labeling a biomolecule in a living system or in a subject, the method comprising: (i) administering to the living system or subject a substrate specific to the biomolecule of interest wherein the substrate comprises a reporter; and (ii) administering to the living system or subject (a) a detectable marker that reacts covalently with the reporter, (b) a tris(triazolylmethyl) amine ligand of formula (I), and (c) Cu(I) or Cu(II) in combination with a reducing agent such as sodium absorbate (to reduce Cu(II) to Cu(I) in situ); wherein the biomolecule of interest is detectably marked. Preferably, the method includes a step (d) of quenching the reaction with a suitable agent sufficient to sequester or chelate copper. Such agents can include, for example, bathocuproine sulphonate (BCS) or bicinchoninic acid (BCA).

The present invention further provides a kit for labeling and/or imaging a biomolecule in vivo, the kit comprising a tris(triazolylmethyl)amine ligand of formula (I). The kit can also comprise a substrate specific to the biomolecule of interest wherein the substrate comprises a reporter, and a detectable marker that binds to the reporter. In addition, the kit can comprise Cu(I) or Cu(II) in combination with a reducing agent such as sodium absorbate (to reduce Cu(II) to Cu(I) in situ). Still further, the kit of the present invention can include a suitable agent sufficient to sequester or chelate copper to quench the reaction. Again, suitable such agents can include, for example, bathocuproine sulphonate (BCS) or bicinchoninic acid (BCA).

The invention further provides a method of synthesizing 2-(4-((bis((1-tert-butyl-1H-1,2,3-triazol-4-yl)methyl) amino)methyl)-1H-1,2,3-triazol-1-yl)ethanesulfonic acid (BTTES) comprising: i) reacting 3,3-diethoxy-1-propyne and tert-butyl azide in a mixture of tert-butyl alcohol and water in the presence of sodium bicarbonate, copper(II) sulfate pentahydrate, and sodium ascorbate to produce 1-tert-butyl-4-(diethoxymethyl)-1H-1,2,3-triazole; ii) combining 1-tert-butyl-4-(diethoxymethyl)-1H-1,2,3-triazole with dichloromethane followed by addition of water and trifluoroacetic acid to produce 1-tert-butyl-1H-1,2,3-triazole-4-carbaldehyde; iii) dissolving 1-tert-butyl-1H-1,2,3-triazole-4-carbaldehyde in dichloroethane or THF followed by addition of propargyl amine and sodium triacetoxyborohydride to produce N,N-bis((1-tert-butyl-1H-1,2,3-triazol-4-yl)methyl)prop-2-yn-1-amine; iv) combining N,N-bis((1-tert-butyl-1H-1,2,3-triazol-4-yl)methyl)prop-2-yn-1-amine with 2-azidoethanol in tetrahydrofuran followed by copper (I) acetate and sodium ascorbate to produce 2-(4-((bis((1-tert-butyl-1H-1,2,3-triazol-4-yl)methyl)amino)methyl)-1H-1,2,3-triazol-1-yl)ethanol; and v) combining 2-(4-((bis((1-tert-butyl-1H-1,2,3-triazol-4-yl)methyl)amino)methyl)-1H-1,2,3-triazol-1-yl)ethanol in pyridine with sulfur trioxide pyridine complex to produce 2-(4-((bis((1-tert-butyl-1H-1, 2,3-triazol-4-yl)methyl)amino)methyl)-1H-1,2,3-triazol-1-yl)ethanesulfonic acid.

DETAILED DESCRIPTION OF THE INVENTION

Figures 1A, 1B, 1C:
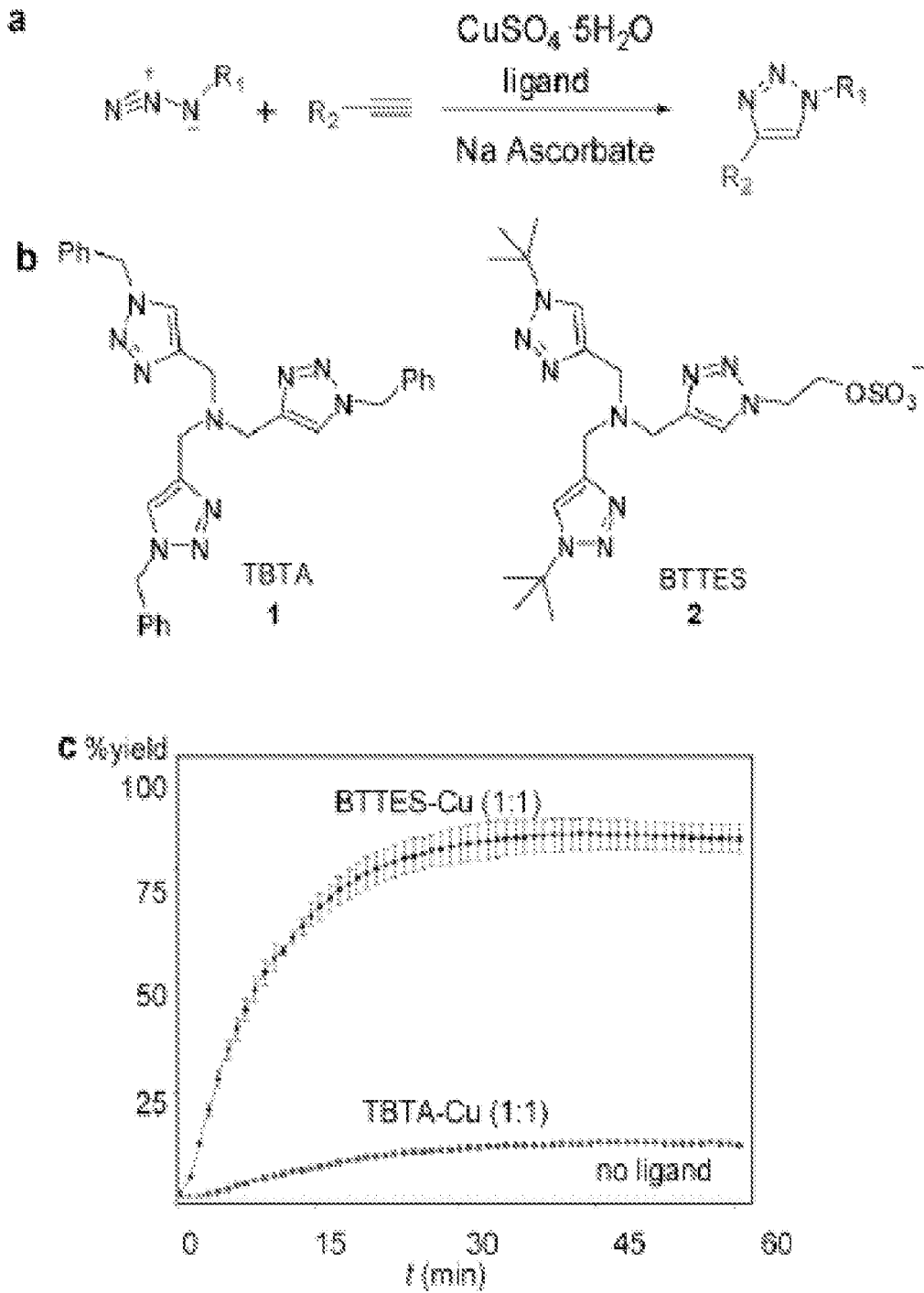
FIG. 1A-1C. Copper(I)-catalyzed azide-alkyne cycloaddition (CuAAC) is accelerated by Cu(I)-stabilizing ligands. (A) CuAAC of azides and terminal alkynes to form 1,4-disubstituted 1,2,3-triazoles. (B) Structures of CuAAC-accelerating ligands. (C) Conversion-time profiles of CuAAC in the presence/absence of accelerating ligands. Reaction conditions: propargyl alcohol (50 µM), 3-azido-7-hydroxycoumarin (100 µM), CuSO$_4$ (75 µM), 0.1 M potassium phosphate buffer (pH 7.0)/DMSO 95:5, sodium ascorbate (2.5 µM), rt. Error bars represent the standard deviation of three replicate experiments.

The present invention provides a Cu(I) ligand for use in an azide-alkyne cycloaddition reaction in a living system or subject wherein the ligand comprises a tris(triazolylmethyl)amine of formula (I):

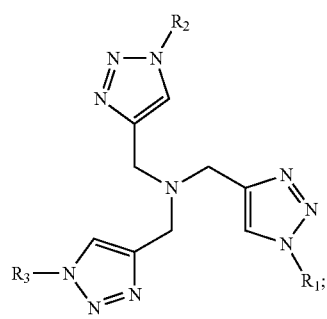

wherein R1 and R2 are independently

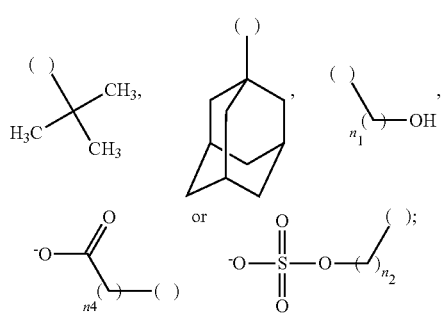

wherein R3 is

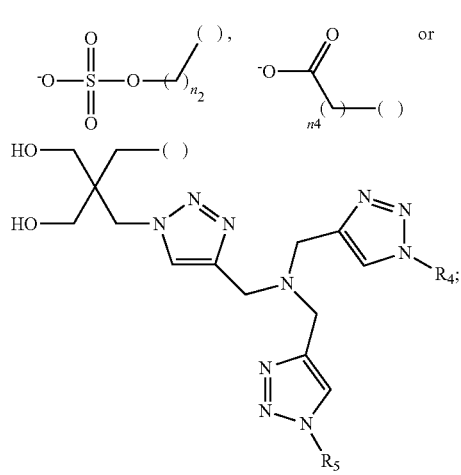

wherein R4 and R5 are independently

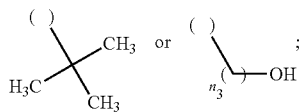

wherein n1, n2 and n3 are independently 2-3, and n4 is 1-2; and wherein ( ) is the point of attachment of the R1, R2, R3, R4 or R5 group to the ring structure.

In one case, the ligand may consist essentially of a tris(triazolylmethyl)amine of formula (I). In another case, the ligand may consist of a tris(triazolylmethyl)amine of formula (I).

In some embodiments, R1 may be the same as R2, and/or R4 may be the same as R5.

The ligand may be any ligand of the disclosed formula. For example, the ligand may comprise

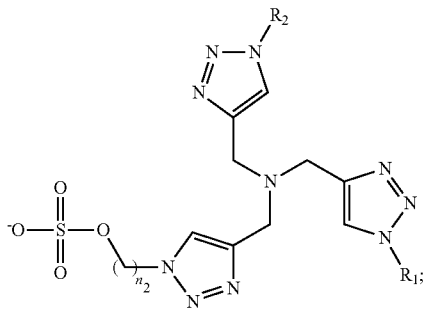

wherein R1 is

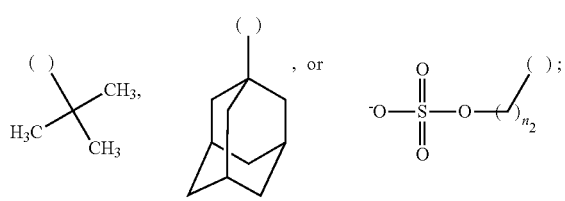

wherein R2 is

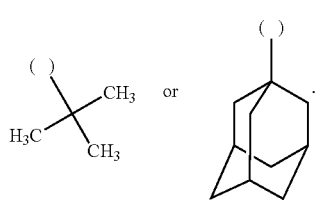

For example, the ligand may be
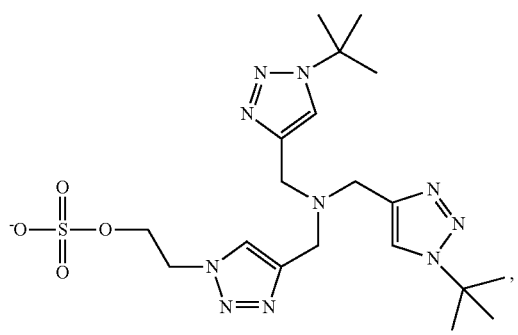
In a more preferred embodiment, the ligand is
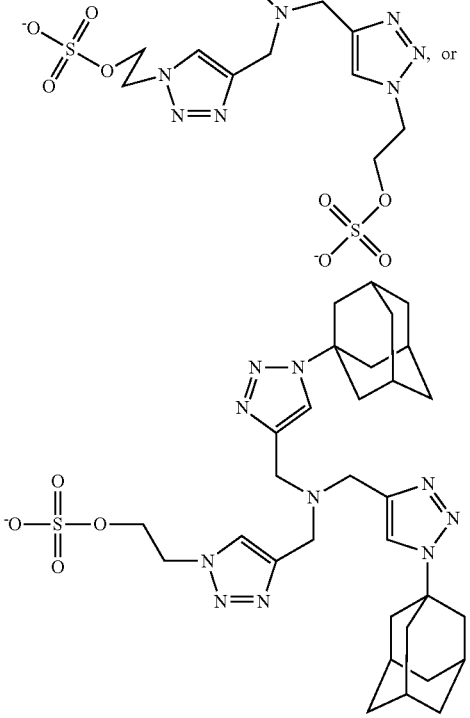
chemical name 2-(4-((bis((1-tert-butyl-1H-1,2,3-triazol-4-yl)methyl)amino)methyl)-1H-1,2,3-triazol-1-yl)ethanesulfonic acid (BTTES).
In another example, the ligand is
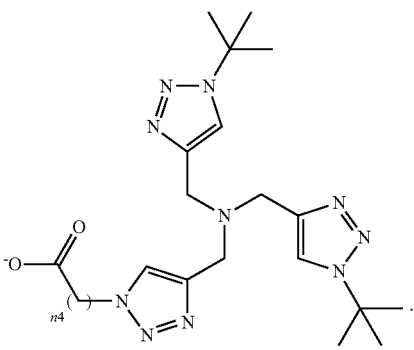
In yet another example, the ligand may comprise
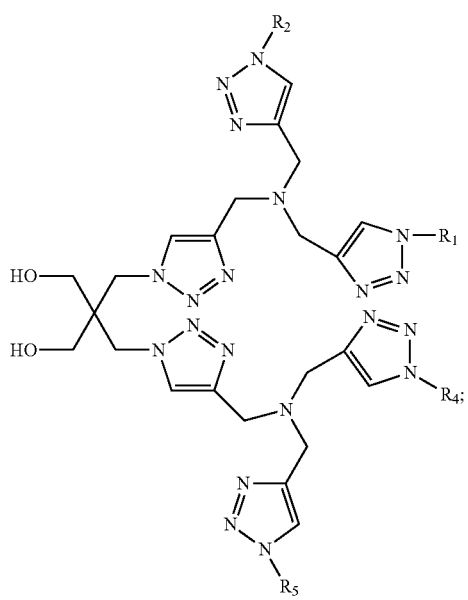
wherein R1 and R2 are independently
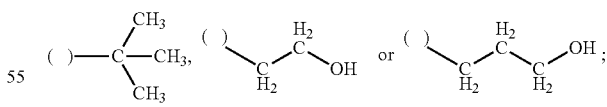
and wherein R4 and R5 are independently
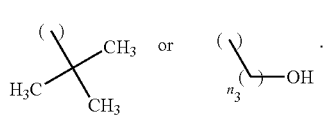
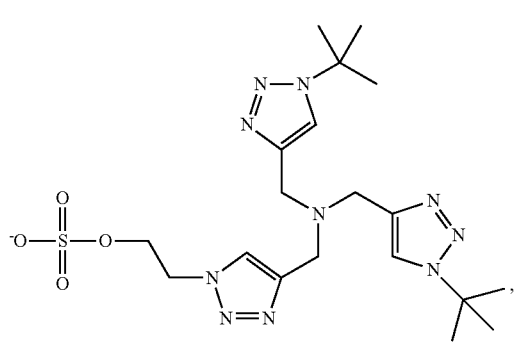

In a preferred embodiment, the ligand is

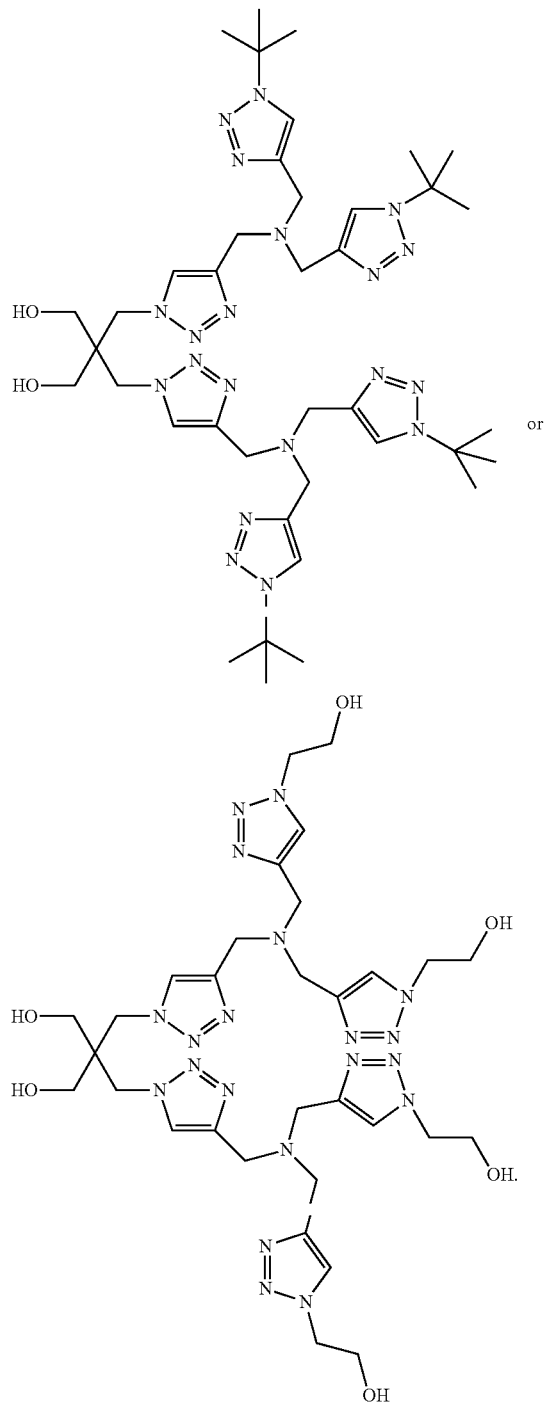

or

The present invention also provides a method of labeling a biomolecule in a living system or in a subject, the method comprising: (i) administering to the living system or subject a substrate specific to the biomolecule of interest wherein the substrate comprises a reporter; and (ii) administering to the living system or subject (a) a detectable marker that reacts covalently with the reporter, (b) a tris(triazolylmethyl) amine ligand of formula (I), and (c) Cu(I) or Cu(II) in combination with a reducing agent such as sodium absorbate (to reduce Cu(II) to Cu(I) in situ); wherein the biomolecule of interest is detectably marked, and wherein the ligand of formula (I) has the structure:

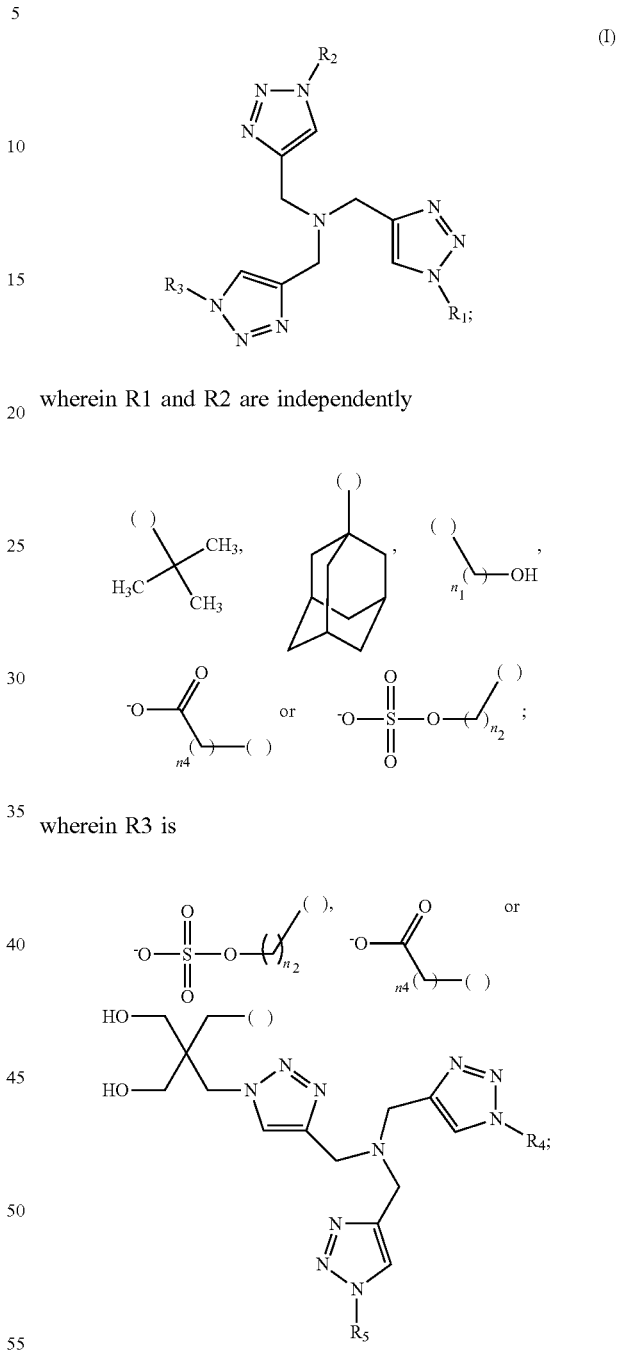

wherein n1, n2 and n3 are independently 2-3, and n4 is 1-2; and wherein ( ) is the point of attachment of the R1, R2, R3, R4 or R5 group to the ring structure.

The method can further comprise detecting the marker. In the method of the present invention, the Cu(I) or Cu(II) in combination with a reducing agent can be administered together, and preferably Cu(I) or Cu(II) is in complex with the ligand. In the most preferred embodiment, the ligand is complexed with CuSO$_4$ and is administered in combination with sodium absorbate to reduce Cu(II) to Cu(I). Preferably, the method includes a step (d) of quenching the reaction with a suitable agent sufficient to sequester or chelate copper. Such agents can include, for example, bathocuproine sulphonate (BCS) or bicinchoninic acid (BCA).

The present invention further provides a kit for labeling and/or detecting a biomolecule in vivo, the kit comprising a tris(triazolylmethyl)amine ligand of formula (I), wherein the ligand of formula (I) has the structure:

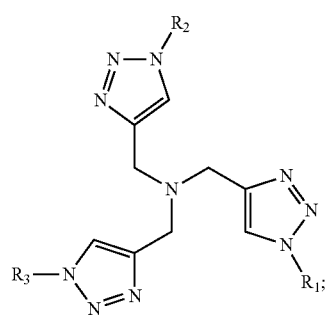
(I)

wherein R1 and R2 are independently

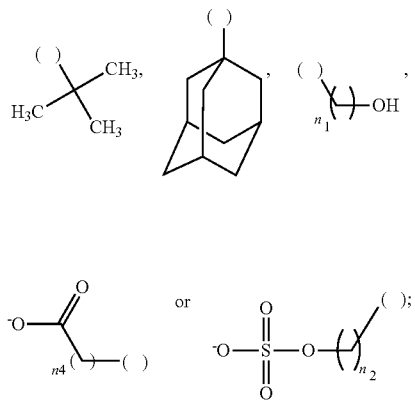

wherein R3 is

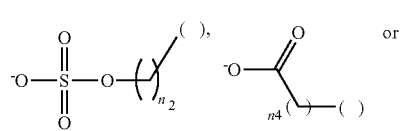

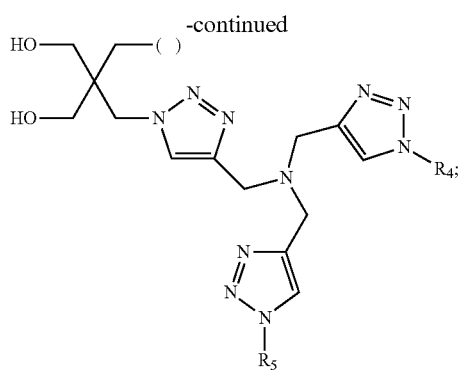
-continued wherein R4 and R5 are independently

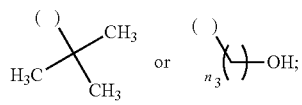

wherein n1, n2 and n3 are independently 2-3, and n4 is 1-2; and wherein ( ) is the point of attachment of the R1, R2, R3, R4 or R5 group to the ring structure.

The kit can also comprise a substrate specific to the biomolecule of interest wherein the substrate comprises a reporter, and/or a detectable marker that covalently reacts to the reporter. In addition, the kit can comprise Cu(I) or Cu(II) in combination with a reducing agent such as sodium absorbate (to reduce Cu(II) to Cu(I) in situ). Still further, the kit of the present invention can include a suitable agent sufficient to sequester or chelate copper to quench the reaction. Again, suitable such agents can include, for example, bathocuproine sulphonate (BCS) or bicinchoninic acid (BCA).

The invention further provides a method of synthesizing 2-(4-((bis((1-tert-butyl-1H-1,2,3-triazol-4-yl)methyl) amino)methyl)-1H-1,2,3-triazol-1-yl)ethanesulfonic acid (BTTES) comprising:

i) reacting 3,3-diethoxy-1-propyne and tert-butyl azide in a mixture of tert-butyl alcohol and water in the presence of sodium bicarbonate, copper(II) sulfate pentahydrate, and sodium ascorbate to produce 1-tert-butyl-4-(diethoxymethyl)-1H-1,2,3-triazole;

ii) combining 1-tert-butyl-4-(diethoxymethyl)-1H-1,2,3-triazole with dichloromethane followed by addition of water and trifluoroacetic acid to produce 1-tert-butyl-1H-1,2,3-triazole-4-carbaldehyde;

iii) dissolving 1-tert-butyl-1H-1,2,3-triazole-4-carbaldehyde in dichloroethane or THF followed by addition of propargyl amine and sodium triacetoxyborohydride to produce N,N-bis((1-tert-butyl-1H-1,2,3-triazol-4-yl)methyl) prop-2-yn-1-amine;

iv) combining N,N-bis((1-tert-butyl-1H-1,2,3-triazol-4-yl)methyl)prop-2-yn-1-amine with 2-azidoethanol in tetrahydrofuran followed by copper(I) acetate and sodium ascorbate to produce 2-(4-((bis((1-tert-butyl-1H-1,2,3-triazol-4-yl)methyl)amino)methyl)-1H-1,2,3-triazol-1-yl)ethanol; and v) combining 2-(4-((bis((1-tert-butyl-1H-1,2,3-triazol-4-yl)methyl)amino)methyl)-1H-1,2,3-triazol-1-yl)ethanol in pyridine with sulfur trioxide pyridine complex to produce 2-(4-((bis((1-tert-butyl-1H-1,2,3-triazol-4-yl)methyl) amino)methyl)-1H-1,2,3-triazol-1-yl)ethanesulfonic acid.

The invention further provides a method of synthesizing 2-(4-((bis((1-tert-butyl-1H-1,2,3-triazol-4-yl)methyl)amino)methyl)-1H-1,2,3-triazol-1-yl)acetic acid (BTTA) comprising: i) combining N,N-bis((1-tert-butyl-1H-1,2,3-triazol-4-yl)methyl)prop-2-yn-1-amine with 2-azidoacetic acid in tetrahydrofuran followed by copper(I) acetate and sodium ascorbate to produce 2-(4-((bis((1-tert-butyl-1H-1,2,3-triazol-4-yl)methyl)amino)methyl)-1H-1,2,3-triazol-1-yl)acetic acid.

Also provided are two compounds synthesized by this method, and two Cu(I) stabilizing ligands for use in an azide-alkyne cycloaddition reaction in a living system or subject wherein the ligand comprises the compound synthesized by the method.

In order to image a biomolecule in vivo, the biomolecule must first be labeled with a detectable marker. In order to give a clear image, the detectable marker must be both specific to the biomolecule of interest and nontoxic to the cell, tissue or subject being imaged. A biomolecule of interest may include, for example, a glycan, such as a glycan attached to a glycoprotein or glycolipid, a lipid, or a protein. In order to obtain biomolecule specificity for the marker, a substrate is administered which is specific to the biomolecule and which contains a reporter, or reactive functional group. Preferably, the reporter, or reactive functional group, is one not naturally found in biological systems, is inert in biological systems, and reacts predictably and with specificity. A detectable marker that reacts covalently to the reporter is administered. Preferably, the detectable marker reacts covalently predictably and with specificity to the reporter and is otherwise inert in biological systems. Such a non-native, non-perturbing chemical that has highly selective reactions with specific chemical groups is termed bioorthogonal (i.e., the two components are non-interacting (orthogonal) to the function of the living system). A bioorthogonal reporter and fluorescent probe will allow predictable, specific reaction between the reporter and the fluorescent probe. For example, azides and alkynes are bioorthogonal, they are not found naturally in biological systems, react with each other predictably, and are otherwise inert in biological systems. The reaction between an azide and alkyne in accordance with the present invention is catalyzed by Cu(I) (i.e., the Cu(I)-catalyzed azide alkyne cycloaddition (CuAAC)). When assisted by a ligand of the present invention, the CuAAC reaction is accelerated. The ligands disclosed in the present invention are nontoxic and biocompatible and can therefore can be used to detect, image and profile biomolecules in vivo. In accordance with the method and kits of the present invention, Cu(I) may be administered, used or employed directly or may be administered, used or employed as Cu(II) together with a reducing agent, so that Cu(II) reduced to Cu(I). In the preferred embodiment, the methods and kits of the present invention administer, use or employ $CuSO_4$ and sodium ascorbate. In one preferred embodiment, a BTTES-$CuSO_4$ complex is used to assist the CuAAC reaction between a substrate with an azide reporter, or reactive functional group, and a fluorescent probe containing an alkyne. As discussed previously, the reaction can be quenched using an agent that sequesters or chelates copper. Such agents include but are not limited to BCS or BCA.

Preferably, the ligand is in complex with Cu(II) as $CuSO_4$ in a ratio of ligand:$CuSO_4$ is 5:1 to 6:1. In a preferred embodiment, the ligand is in a 6:1 ligand-$CuSO_4$ complex.

Once the probe has reacted with the reporter, the biomolecule of interest can be detected or the distribution of the biomolecule can be analyzed or profiled. Certain disease states, such as certain cancers, have biomolecular markers that are elevated or specific to the disease state. A cell in the disease state may present with certain specific biomolecular markers. For example, certain prostate cancers present with a highly N-Acetylgalactosamine-enriched glycome, relative to non-disease cells. As a further example, certain other cancers present with highly sialic acid- or fucose-enriched glycomes, relative to non-disease cells. This allows the imaging of the biomolecular marker in the subject or the analysis or profile of the biomolecular marker and may allow a determination of the prevalence or distribution of diseased cells in the subject.

The subject of the present invention can be any vertebrate. More preferably, the subject is a mammal such as a rodent (e.g., mouse, rat) or a human.

The biomolecules of interest or biomolecular marker of the disease state can be any biomolecule, for example, a lipid, a protein, a nucleic acid or a glycan in the form of a glycoprotein or a glycolipid. The glycan may comprise, for example, sialic acid, fucose or N-Acetylgalactosamine.

The substrate can be any chemical or biological agent that can serve as a metabolic precursor, for example, a monosaccharide, monosaccharide analog, lipid, lipid analog, monomeric nucleotide, monomeric nucleotide analog, amino acid, or amino acid analog. Preferably, the substrate is preferentially incorporated into the biomolecule of interest via metabolic, genetic, or synthetic approaches. For example, when the biomolecule of interest or biomolecular marker of the disease state is a glycan attached to a glycoprotein or glycolipid, the reporter can, for example, be any sugar analogue that can be incorporated into the synthesis of the glycan. The sugar can be an analogue of any known monosaccharide, including but not limited to, sialic acid, fucose, N-Acetylgalactosamine, glucuronic acid, or N-Acetylglucosamine. The analogue can have any reactive functional group, for example, an azide or a terminal alkyne. For example, the substrate can be azide- or alkyne-bearing GDP-fucose, CMP-Sia, GalNAc, or $Ac_4ManNAc$. In one example, when the biomolecular marker of the disease state is a fucose-enriched glycome, GDP-FucAl, an alkyne-bearing GDP-fucose analogue, is administered. The GDP-fucose will be preferentially taken up by the disease cells and will be incorporated into the glycome. After addition of the fluorescent probe and the ligand disclosed, the disease cells with the biomolecular marker of the disease state will be preferentially fluorescently labeled. When the biomolecule of interest or biomolecular marker of the disease state is a protein, the substrate can, for example, be an amino acid analogue that can be incorporated into the synthesis of the protein via metabolism.

Once the substrate has been incorporated into the synthesis of, the biomolecule of interest or the biomolecular marker of the disease state, a detectable marker that reacts covalently with the reporter may bind to the biomolecule of interest. The detectable marker used in connection with the ligands, methods and kits of the present invention may be any detectable marker known in the art and include, for example, a fluorescent probe, an affinity probe, or a radiolabeled probe. Preferably, the detectable marker is a fluorescent probe. The detectable marker can react with the reporter in any manner known in the art. Preferably, the reaction is bioorthogonal. For example, if the reporter is an azide, the detectable marker can have an alkyne functional group. In another example, if the reactive functional group is an alkyne, the detectable marker can have an azide functional group. The detectable marker can be any azide- or alkyne-conjugated detectable marker known in the art, such as an azide- or aklyne-conjugated fluorescent, affinity, or radio probe.

The biomolecule of interest can be detected by any method known in the art, for example, if the detectable marker is a fluorescent probe, the biomolecule of interest can be detected by fluorescent microscopy. In another example, if the detectable marker is an affinity probe, the biomolecule of interest can be detected by electrophoresis.

EXPERIMENTAL DETAILS

Example I

1. Materials and Methods

All chemical reagents and solvents were obtained from Sigma-Aldrich and Acros and used without further purification unless otherwise noted. Flash chromatography was performed using a Sorbent 60 Å 230- to 400-mesh silica gel. Analytical thin layer chromatography (TLC) was performed on glass-backed Analtech Uniplate silica gel plates, and compounds were visualized by staining with p-anisaldehyde or phosphomolybdic acid or $KMnO_4$ stain. Organic extracts were dried over anhydrous $MgSO_4$ or $Na_2SO_4$, and the drying agent was removed by gravity filtration. Unless otherwise specified, all solvents were removed under reduced pressure, using a rotary evaporator. Rhodamine-dextran, Alexa Fluor dye-conjugated azides and alkynes were purchased from Invitrogen. Frosted Microscope Slides and wide-bore Pasteur pipets were purchased from Fisher Scientific and 18×18 mm square cover glasses were purchased from Corning. Melting point (m.p.) was taken on a Melt-Temp (Laboratory Device USA) apparatus using a Traceable® digital thermometer without calibration. HPLC purifications were performed using a LC-6AA Shimadzu high performance liquid chromatographer equipped with a SPD-M20A Prominence Diode Array Detector. NMR spectra were obtained with Bruker DRX 300 and 600 spectrometers. $^1H$ chemical shifts (δ) are referenced to residual protic solvent ($D_2O$, 4.79 ppm; $CDCl_3$, 7.26 ppm) and coupling constants (J) are reported in hertz (Hz). $^{13}C$ NMR spectra were recorded at 75 MHz and proton decoupled. Electrospray ionization mass spectra (ESI-MS) were obtained at the Albert Einstein Laboratory for Macromolecular Analysis and Proteomics. Kinetic measurements using propargyl alcohol and 3-azido-7-hydroxy-coumarin as the model system were optimized using a 96-well BioTek Synergy Hybrid Plate Reader. Microinjections were performed using a PV 820 Pneumatic PicoPump (World Precision Instruments) under Nikon SMZ1500 with lens Plan Apo 1×WD70.

Flow Cytometry:

Flow cytometry experiments were performed on a Becton Dickinson FACScan analog bench top analyzer flow cytometer using a 488 nm argon laser. At least 18000 cells were recorded for each sample. Flow cytometry data were analyzed using Flowjo. Mean fluorescence intensity (MFI) was calculated for live cells. Cell viability was ascertained by gating the sample on the basis of forward scatter (to sort by size) and FL3 (to sort by 7-AAD negative).

Image Acquisition and Analysis:

Fluorescent and brightfield images of cells and zebrafish embryos were acquired on Nikon Eclipse Ti epifluorescence microscope with 4×/0.10 lens. Images acquired were processed using NIS-Elements AR 3.10. Whole animal images were acquired with an Olympus SZ16 fluorescent or SZ61 dissecting microscope equipped with a digital camera and pictureframe software. Confocal fluorescent images were acquired sequentially on a Leica SP5 AOBS confocal microscope with a 10×/0.4 air objective. Either a 488 nm diode laser with a 505-550 nm bandpass filter for Alexa Fluor 488 or a 633 nm diode laser with 660-720 nm bandpass filter for Alexa Fluor 647 was used. All embryo images were acquired using a 5 μm step size and 1 airy unit. Composite figures were prepared using ImageJ, Photoshop CS2 and Illustrator CS2 software (Adobe). Movies were assembled using ImageJ.

Tissue Culture/Cell Growth Conditions:

Jurkat and LNCaP cells were grown in RPMI 1640 medium supplemented with 10% FCS (Sigma). HEK 293T cells were grown in Dulbecco's modified Eagle's medium supplemented with 10% FCS. Pro⁻5 CHO cells were grown in suspension or monolayer in alpha-Minimum Essential medium supplemented with 10% FCS. In all cases, cells were incubated in a 5.0% carbon dioxide, water-saturated incubator at 37° C.

Zebrafish Husbandry and Strains:

Casper mutant (a double mutant line that lacks melanocytes and iridophores described previously [43]) or AB/Tü wild-type strains were used in this study. Clutches of homozygous double mutant (casper) embryos were obtained by intercrossing homozygous adults that are double for mutations in nacre [42], and roy orbison (roy) [43].

Synthetic Procedures

Ac₄ManNAc [45], Ac₄ManNAl [46], Ac₄ManNAz [45], CMP-Sia [47], CMP-SiaNAz [47], CMP-SiaNAl [47], GDP-Fuc [48], GDP-FucAl [48], biotin-azide [49], biotin-alkyne [50], tert-butyl azide [51] were synthesized as previously described. DIFO-647 was a gift from Professor Carolyn Bertozzi. All final compounds were purified by either reverse phase HPLC or Bio-Gel P2 gel (Bio-Rad) filtration chromatography.

Figure 11:
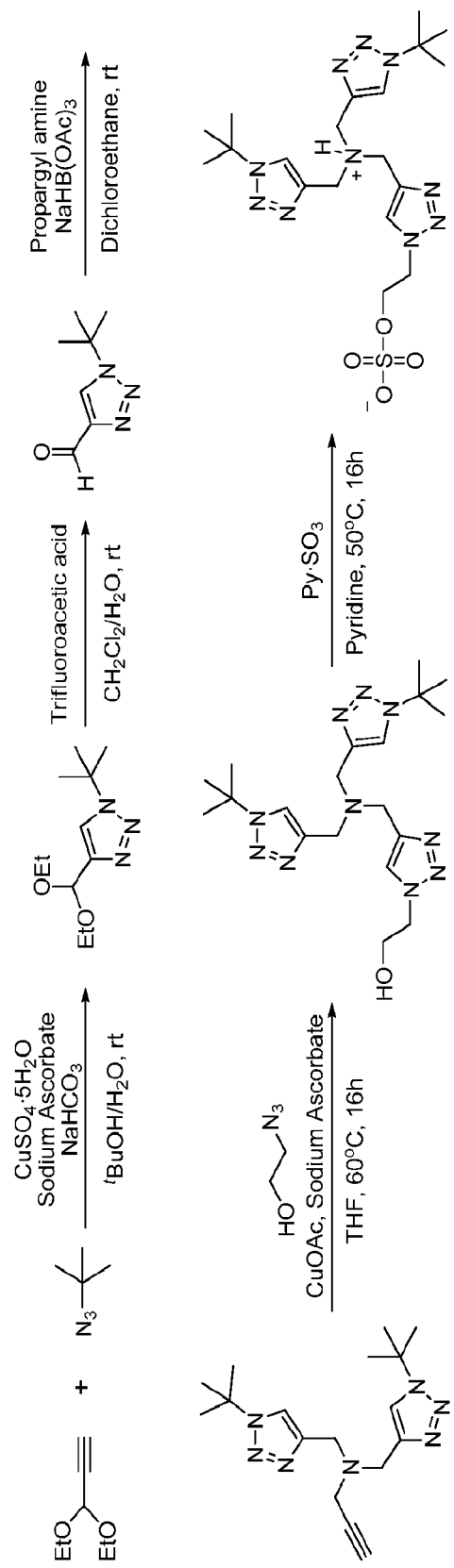
FIG. 11. Synthesis scheme of BTTES. THF=tetrahydrofuran.

Synthesis of 1-tert-butyl-4-(diethoxymethyl)-1H-1,2,3-triazole (FIG. 11)

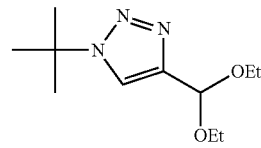 [SMILES: CCOC(OCC)c1cn(C(C)(C)C)nn1]

To a 20-mL screw-capped scintillation vial equipped with a stirring bar were added 3,3-diethoxy-1-propyne (1.50 g, 11.8 mmol, 1.0 eq) and tort-butyl azide (1.34 g, 13.5 mmol, 1.15 eq) in 10 mL 1:1 mixture of tert-butyl alcohol and water. Sodium bicarbonate (1.40 g, 16.7 mmol, 1.41 eq), copper(II) sulfate pentahydrate (0.143 g, 0.57 mmol, 5.0 mol %), and sodium ascorbate (0.47 g, 2.35 mmol, 20 mol %) were added to the mixture. The reaction was stirred vigorously overnight, and TLC analysis indicated the formation of a new product ($R_f$=0.7 in ethyl acetate, $KMnO_4$ stain). EDTA (2 mL, 0.5 M, pH=8) was added, the reaction mixture was diluted with EtOAc (90 mL), washed with sat aq $NaHCO_3$ (2×50 mL), water (2×10 mL), and brine (30 mL). The combined organic phases were dried over anhydrous $MgSO_4$, filtered, and concd in vacuo to provide 2.54 g of a light yellow oil (yield: 95%). The crude product was used without further purification. $^1H$ NMR (300 MHz, $CDCl_3$) δ 7.64 (s, 1H), 5.71 (s, 1H), 3.78-3.60 (m, 4H), 1.67 (s, 9H), 1.25 (t, J=7.0 Hz, 6H); $^{13}C$ NMR (75 MHz, $CDCl_3$) 146.5, 118.9, 97.2, 61.9, 59.4, 30.1, 15.2; HRMS cacld for [M+Na]+ C$_{11}$H$_{21}$N$_3$NaO$_2$ 250.1531. found 250.1531.

Synthesis of 1-tert-butyl-1H-1,2,3-triazole-4-carbaldehyde

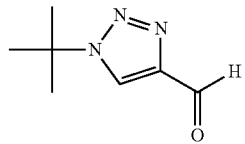

To a 50-mL round bottom flask was added a solution of 1-tert-butyl-4-(diethoxymethyl)-1H-1,2,3-triazole (1.28 g, 5.63 mmol) in dichloromethane (6.0 mL), followed by addition of water (3.0 mL) and trifluoroacetic acid (1.0 mL). The reaction was stirred vigorously under nitrogen for 3 h until TLC analysis indicated the complete disappearance of the starting material (10% EtOAc in dichloromethane, starting material R$_f$ 0.5, product R$_f$ 0.6, KMnO$_4$ stain). The reaction mixture was diluted with EtOAc (100 mL), washed with sat aq NaHCO$_3$ (3×40 mL) and brine (40 mL). The combined organic phases were dried over anhydrous MgSO$_4$, filtered, and concd in vacuo to provide 0.71 g of a light yellow oil (yield: 82%). The crude product was used without purification.

Synthesis of N,N-bis((1-tert-butyl-1H-1,2,3-triazol-4-yl)methyl)prop-2-yn-1-amine

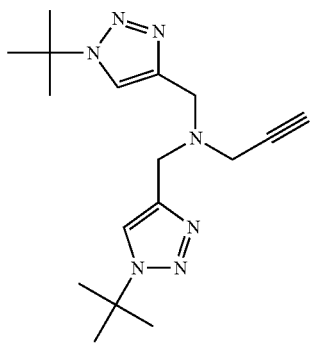 [SMILES: C#CCN(Cc1cn(C(C)(C)C)nn1)Cc1cn(C(C)(C)C)nn1]

To a 250-mL round bottom flask was added a solution of 1-tert-butyl-1H-1,2,3-triazole-4-carbaldehyde (2.47 g, 16.1 mmol, 2.2 eq) in 84 mL dichloroethane (~0.2 M), followed by addition of propargyl amine (361 mg, 7.2 mmol, 1.0 eq). To this mixture sodium triacetoxyborohydride (3.8 g, 17.9 mmol, 2.5 eq) was added in one portion with vigorous stirring. The reaction mixture was stirred at rt for 40 h. 1N H$_2$SO$_4$ (86 mL) was added to the reaction, and the mixture was stirred for 15 min. The pH was adjusted to >10 by addition of potassium carbonate. The reaction mixture was diluted with 100 mL of water and extracted with dichloromethane (3×300 mL). The organic layers were combined, dried over anhydrous MgSO$_4$, filtered, and concd in vacuo to provide a crude product. Further purification by flash chromatography (100 g silica gel, 20% hexanes in EtOAc, R$_f$ 0.2, KMnO$_4$ stain) provided 1.98 g of product (yield: 84%) as a white powder. mp 125.5-126.1° C.; $^1$H NMR (300 MHz, CDCl$_3$) δ 7.67 (s, 2H), 3.87 (s, 4H), 3.40 (d, J=2.4 Hz, 2H), 2.28 (t, J=2.4 Hz, 1H), 1.67 (s, 18H); $^{13}$C NMR (75 MHz, CDCl$_3$) δ 143.6, 120.2, 78.8, 73.5, 59.2, 47.8, 42.2, 30.0; HRMS cacld for [M+H]+ C$_{17}$H$_{28}$N$_7$ 330.2406. found 330.2400.

Synthesis of 2-(4-((bis((1-tert-butyl-1H-1,2,3-triazol-4-yl)methyl)amino)methyl)-1H-1,2,3-triazol-1-yl)ethanol

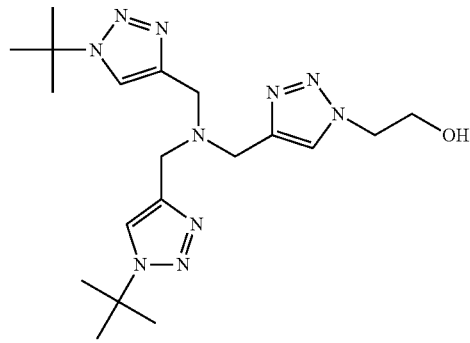 [SMILES: CC(C)(C)n1cc(CN(Cc2cn(CCO)nn2)Cc2cn(C(C)(C)C)nn2)nn1]

To a 20-mL screw-capped vial equipped with a stirring bar were added N,N-bis((1-tert-butyl-1H-1,2,3-triazol-4-yl)methyl)prop-2-yn-1-amine (1 g, 3.04 mmol, 1.0 eq) and 2-azidoethanol (304 mg, 3.49 mmol, 1.15 eq) in 16 mL of THF. To the mixture were added copper(I) acetate (20 mg, 0.16 mmol, 5.0 mol %) and sodium ascorbate (130 mg, 0.66 mmol, 20 mol %). The reaction mixture was stirred vigorously with the cap closed at 60° C. overnight. To the reaction mixture were added 2 mL water and ~0.2 g CupriSorb™. The mixture was stirred for 30 additional min and then filtered. The crude product was concd in vacuo and was purified by HPLC (solvent A: 0.1% TFA in H$_2$O; solvent B: 0.1% TFA in acetonitrile; method: 20% B to 100% B over 20 min). HPLC fractions containing the product (RT: 14 min-15.5 min) were combined and lyophilized to provide 1.2 g (95%) of product as a tan solid. mp 82.0-83.0° C.; $^1$H NMR (300 MHz, D$_2$O) δ 7.94 (s, 2H), 7.92 (s, 1H), 4.51 (t, J=5.1 Hz, 2H), 4.51 (t, J=5.2 Hz, 2H), 3.83 (s, 2H), 3.82 (s, 4H), 1.61 (s, 18H); $^{13}$C NMR (75 MHz, CDCl$_3$) δ 143.9, 143.3, 125.9, 123.0, 60.7, 60.5, 52.9, 48.4, 39.1, 29.3; HRMS cacld for [M+H]+ C$_{19}$H$_{33}$N$_{10}$O 417.2839. found 417.2839.

Synthesis of 2-(4-((bis((1-tert-butyl-1H-1,2,3-triazol-4-yl)methyl)amino)methyl)-1H-1,2,3-triazol-1-yl)ethanesulfonic acid (BTTES, 2)

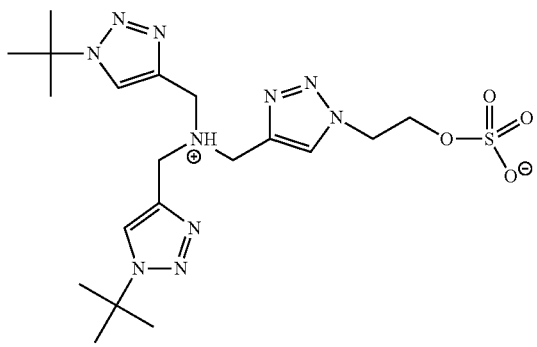 [SMILES: CC(C)(C)n1cc(C[NH+](Cc2cn(CCOS(=O)(=O)[O-])nn2)Cc2cn(C(C)(C)C)nn2)nn1]

To a solution of 2-(4-(((bis((1-tert-butyl-1H-1,2,3-triazol-4-yl)methyl)amino)methyl)-1H-1,2,3-triazol-1-yl)ethanol (100 mg, 0.24 mmol, 1.0 eq) in 5 mL of pyridine (~0.05 M) was added sulfur trioxide pyridine complex (190 mg, 1.2 mmol, 5.0 eq). The reaction was stirred at 50° C. under argon overnight. Upon cooling to room temperature 1 mL of methanol was added. Stirring continued for an additional 30 min. The volatiles were then removed in vacuo to yield a solid that was purified via HPLC (solvent A: 0.1% TFA in H$_2$O; solvent B: 0.1% TFA in acetonitrile; method: 20% B to 100% B over 20 min). HPLC fractions containing the product (RT: 14 min-15.5 min) were pooled and lyophilized to provide 86 mg of 2 white powder (75%). mp 160° C. (dec); $^1$H NMR (300 MHz, D$_2$O) δ 7.99 (s, 1H), 7.96 (s, 2H), 4.73 (d, J=4.8 Hz, 2H), 4.41 (d, J=4.8 Hz, 2H), 3.84 (s, 2H), 3.81 (s, 4H), 1.62 (s, 18H); $^{13}$C NMR (75 MHz, D$_2$O) δ 143.8, 143.3, 126.2, 123.0, 67.0, 60.6, 50.0, 48.4, 48.2, 29.3; HRMS cacld for [M+H]$^+$ C$_{19}$H$_{33}$N$_{10}$O$_4$S 497.2407. found 497.2437.

A pH 7, 20 mM solution of the HPLC purified BTTES was prepared by dissolving the material in water, and neutralizing with NaOH. This stock was used for all kinetics and in vivo labeling experiments.

Synthesis of 2-(4-(((bis((1-tert-butyl-1H-1,2,3-triazol-4-yl)methyl)amino)methyl)-1H-1,2,3-triazol-1-yl)acetic acid

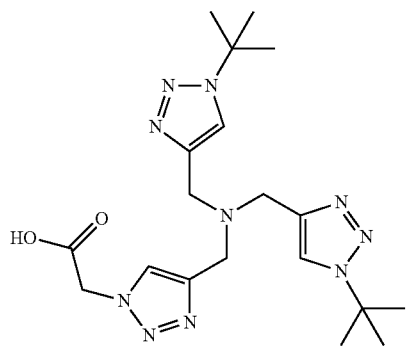 [SMILES: CC(C)(C)n1cc(CN(Cc2cn(CC(=O)O)nn2)Cc2cn(C(C)(C)C)nn2)nn1]

To a 20-mL screw-capped vial equipped with a stirring bar were added N,N-bis((1-tert-butyl-1H-1,2,3-triazol-4-yl)methyl)prop-2-yn-1-amine (109 mg, 0.33 mmol, 1.0 eq) and 2-azidoacetic acid (50 mg, 0.50 mmol, 1.5 eq) in 3 mL of THF. To the mixture were added N,N'-diisopropylethylamine (68 mg, 0.53 mmol, 1.6 eq) tris(triphenylphosphine)copper(I) bromide (31 mg, 0.033 mmol, 10 mol %). The reaction mixture was stirred vigorously with the cap closed at 60° C. overnight. To the reaction mixture were added 2 mL water and ~0.2 g CupriSorb™. The mixture was stirred for 30 additional min and then filtered. The crude product was concd in vacuo and was purified by flash chromatography (25 g silica gel, 40% MeOH in EtOAc with 1% acetic acid, R$_f$ 0.2, KMnO$_4$ stain) to provide 109 mg of product (yield: 76%) as a white solid. $^1$H NMR (300 MHz, D$_2$O) δ 8.22 (s, 2H), 8.14 (s, 1H), 5.10 (s, 2H), 4.72 (s, 2H), 4.39 (s, 4H), 1.66 (s, 18H).

Protocol for Kinetic Measurement of CuAAC of 3-azido-7-hydroxy-coumarin and Propargyl Alcohol [52]

Stock solutions: CuSO$_4$: 10 mM in water, 100 mM in water; Ligand: for single tetrahedral chelation 20 mM (in water), for double tetrahedral chelation 10 mM in water; Sodium ascorbate: 25 mM in water; Coumarin-N$_3$: 100 mM, 10 mM, and 1.0 mM in DMSO; Propargyl alcohol: 100 mM, 10 mM, and 1.0 mM; Buffer: 500 mM potassium phosphate pH 7.0.

Final concentrations: Buffer: 100 mM potassium phosphate pH 7.0; Coumarin-N$_3$: 0.10 mM in DMSO; Propargyl alcohol: 0.05 mM; CuSO$_4$: as desired between 50 and 100 μM, mostly 75 μM; Ligand: ligand to copper ratio is 1:1, 2:1, 3:1, 4:1, 5:1, 6:1, 7:1; DMSO: 5% vol; Sodium ascorbate: 2.5 mM.

Procedure for 200 μL reactions: In a 96-well fluorescence plate, add the reagents in the following order: (1) 40 μL of 500 mM phosphate buffer pH 7.0; (2) 1.0 μL 10 mM propargyl alcohol; (3) 10 μL of DMSO; (4) 6 μL of premixed CuSO$_4$ and ligand ([Cu]=2.5 mM); (5) 1.0 μL 20 mM coumarin-N$_3$; (6) 20 μL of 25 mM sodium ascorbate; (7) Read fluorescence (λ$_{ex}$=404 nm, λ$_{em}$=477 nm, RFU) on the Synergy plate reader.

AlamarBlue Cell Viability and Cell Growth Assay

Jurkat and HEK 293T cell were cultured in medium or medium containing 50 μM Ac$_4$ManNAz or Ac$_4$ManNAl. After 72 hours all cells were harvested, with HEK cells harvested by trypsinization (Trypsin EDTA, 1×). Cells were washed twice with 10 mL PBS (1% FBS) and resuspended in the same buffer with a final concentration of 1 M viable cells per 100 μL. Cells cultured with Ac$_4$ManNAz were reacted with or without biotin-alkyne and cells cultured with Ac$_4$ManNAl were reacted with or without biotin-azide in a 100 μL reaction containing 75 μM CuSO$_4$, 450 μM BTTES, and 2.5 mM freshly prepared sodium ascorbate at rt. As a positive apoptosis control to determine the copper toxicity in the absence of the ligand, cells (cultured in the absence of the unnatural sugars) were reacted with 75 μM CuSO$_4$ and 2.5 mM sodium ascorbate. After 3 min all reactions were quenched with BCS (1 mM). Untreated cells cultured in medium or medium containing Ac$_4$ManNAz or Ac$_4$ManNAl were included as negative controls. Following the reactions cells were washed twice with 0.5 mL PBS (1% FBS) and once with 0.5 mL complete media. Cells were resuspended in 1 mL complete media and total cell numbers were determined. In most cases, ~75% cells were recovered. All cells were then normalized to the lowest concentration. Cell viability was determined by AlamarBlue colorimetric assay (Invitrogen). Briefly, treated or untreated Jurkat were seeded at 80,000 cells/100 μL complete media, and HEK 293T cells were seeded at 10,000 cells/100 μL complete media. AlamarBlue stock solution was diluted to 10% and incubated with the Jurkat cells and HEK 293T cells for 6 and 20 h respectively, at which time the percentage of the reduced form of resorufin (alamarBlue) reached ~50% (the percentage of the reduced form of resorufin is proportional to cell viability). The absorbance of resorufin was measured at 540 (Red) and 600 (Ox) nm. To determine cell growth following the reaction, Jurkat and HEK 293T cell were seeded at 60,000 cells/mL and 125,000 cells/mL, respectively. The viable cells were counted every 24 hours for 3-4 days using Trypan blue dye exclusion method.

Labeling of Alkynyl or Azido Sialic Acids on Mammalian Cell Surface with Biotinylated Probes Via CuAAC and Analyzing by Flow Cytometry Jurkat, CHO, HEK and LNCaP cells were incubated for 3 days in untreated medium or medium containing 50 μM Ac$_4$ManNAz or Ac$_4$ManNAl. The cells then were distributed into a 96-well round bottom tissue culture plate (0.4-0.5 million cells/well), pelleted (300 × g, 3 min), and washed 2 × with 200 μL of labeling buffer (PBS, pH 7.4, containing 1% FCS). Cells were then resuspended in 92 µL labeling buffer, followed by addition of 100 µM biotin-alkyne (for azide bearing cells) or biotin-azide (for alkyne-bearing cells), 2.5 mM sodium ascorbate and BTTESCuSO$_4$ complex (CuSO$_4$ concentrations from 20 µM to 75 µM, BTTES-CuSO$_4$ ratio from 5:1 to 7:1) in labeling buffer at room temperature. The reactions were quenched by adding 2 µL of copper chelator BCS (50 mM) at various time point. Then the cells were pelleted, washed 3 x with labeling buffer, and resuspended in the same buffer containing 1 µg/mL streptavidin-Alexa Fluor 488 conjugate (Invitrogen). After a 30-min incubation on ice (in the dark), the cells were washed 3 x with 200 µL of cold labeling buffer, and then resuspended in 400 µL FACS buffer (Hank's Balanced Salt Solution, pH=7.4, 1% BCS, 2 µg/mL 7-AAD, 0.2% NaN$_3$) for flow cytometry analysis.

Metabolic Labeling of Zebrafish Embryos by Microinjection with GDPFucAl and Detection by the BTTES-Cu(I) or BTTA-Cu(I) Catalyzed Click Chemistry Zebrafish embryos at the one-cell or two-cell stage were microinjected in the yolk with 1 nL of a 20 mM solution of GDP-FucAl (or GDP-fucose) and either rhodamine-dextran (5% w/v) or phenol red (0.1% w/v) in 0.2 M KCl as a tracer. The embryos were allowed to develop to 5 hpf, at which point they were manually dechorionated. The dechorionated embryos were cultured in E3 embryo medium at 28° C. for an additional 3 h before transferring to 1% agarose-coated 96-well plates containing 92 µL embryo medium using a fire-polished wide-bore Pasteur pipette. Alexa Fluor-488 azide (100 µM from a 1.75 mM stock in H$_2$O) was added to each well, followed by BTTES-CuSO$_4$ or BTTA-CuSO$_4$ 6:1 complex ([Cu]=50 µM from 2.5 mM stock). The solutions were gently shaken, and freshly prepared sodium ascorbate (2.5 mM from 100 mM stock in embryo medium) was added to initiate the click reactions. After 1 (BTTA-CuSO$_4$) or 3 min (BTTES-CuSO$_4$), the reaction was quenched with BCS (1 mM from 50 mM stock in water) and diluted immediately with 100 µL embryo medium. The treated embryos were washed 2 x with 15 mL embryo medium and were anesthetized with 0.2% (w/v) Tricaine in embryo medium. After mounting on a slide or 50 mm glass bottom dishes (Matek) in 1.5-3% methyl cellulose and E3 medium, the embryos were ready for imaging by confocal microscopy.

2. Results

In nature copper is a bioessential element and the second most abundant transition metal in the human organism [24]. With Cu(II)/Cu(I) redox potential between 0.0 to 0.8 V, copper containing enzymes are prevalent, participating particularly in reactions involving dioxygen transport and utilization [24-27], as well as in the degradation of unwanted side products of O$_2$ metabolism such as O$_2^-$ radicals [28]. The activities of these enzymes are elegantly orchestrated by the ligands surrounding the copper ions in the active sites. Applying lessons from nature, it was sought to design a new ligand for Cu(I) that could extend the utilization of CuAAC to living systems. When coordinating with Cu(I), the ligand would engage in forming an active copper catalyst to promote the azide-alkyne cycloaddition at micromolar Cu(I) concentrations, while sequestering the copper-associated cytotoxicity.

To develop an air-stable and non-toxic Cu(I) catalyst that is suitable for applications in living systems, a library of 14 water soluble TBTA analogues was screened (Table 1). A ligand, BTTES, was identified, which dramatically accelerated the rate of the azide-alkyne cycloaddition by coordination with the in situ generated Cu(I) (FIG. 1B, 1C). In a fluorogenic assay, 75 µM of CuSO4 premixed with the ligand at various ratios (between 2:1 to 6:1, [ligand]:[copper]) yielded >50% cycloaddition product within 15 min. In contrast, the TBTA-Cu(I)-catalyzed reaction was significantly slower, leveling off with <20% yield, and the reaction rate decreased gradually when more than one equivalent of the ligand was used.

Biocompatibility Evaluation of the BTTES-Cu(I) Complex

As the first step toward extending the use of CuAAC to living systems, it was sought to evaluate the cytotoxicity of the new ligand-copper complex by 7-aminoactinomycin D (7-AAD) staining and flow cytometry analysis. Jurkat cells, a human T lymphocyte cell line, were incubated with 50 µM peracetylated N-(4-pentynoyl)mannosamine (Ac$_4$ManNAl) or peracetylated N-azidoacetylmannosamine (Ac$_4$ManNAz) to introduce the corresponding sialic acid (SiaNAl or SiaNAz) into their cell-surface glycoconjugates. Three days later, the cells were reacted with biotin-azide (or biotin-alkyne, 100 µM), sodium ascorbate (2.5 mM) and CuSO$_4$ (25-75 µM) premixed with BTTES or in the absence of BTTES. The reactions were quenched after 5 min with bathocuproine sulphonate (BCS), a biocompatible copper chelator [29]. Significant cell death was observed when the cells were treated with the in situ generated Cu(I) alone, and cell death increased along with increasing copper concentration. Interestingly, it was observed that cells bearing alkynes on their surface underwent apoptosis much faster than their azide-bearing counterparts, presumably due to the formation of the reactive Cu(I)-acetylide on their surface. In stark contrast, when cells were treated with the BTTES-Cu(I) complexes, cell death decreased dramatically. In the presence of BTTES-Cu(I) 6:1 complex, cell death was completely suppressed to the same level as untreated cells. Similar results were obtained using Chinese Hamster Ovary (CHO) cells.

Figures 2A, 2B, 2C, 2D:
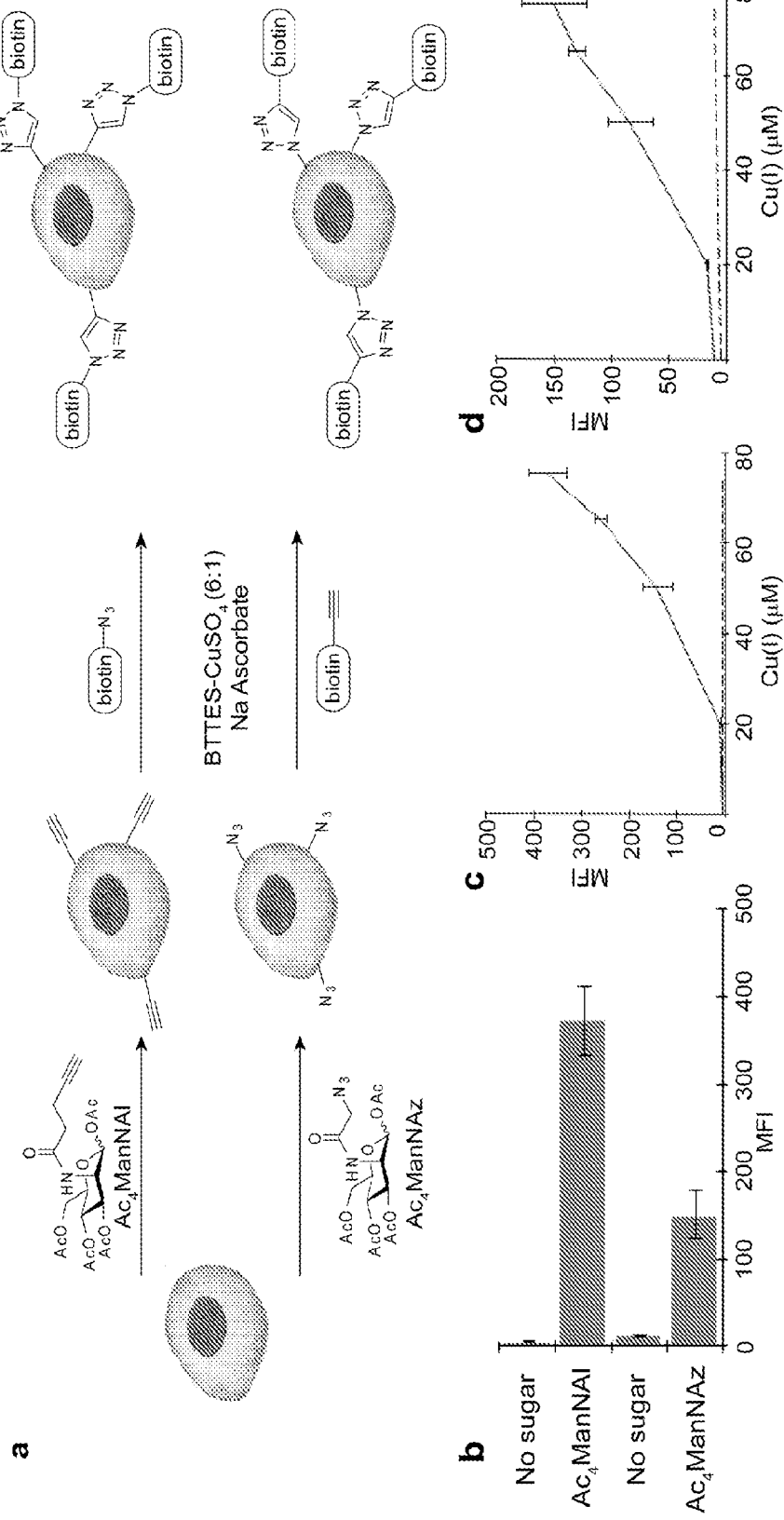
FIG. 2A-2D. Detection of glycoconjugates on the surface of live cells via biocompatible CuAAC. (A) Schematic representation of metabolic labeling and detection of cell-surface sialic acids using Ac$_4$ManNAl and Ac$_4$ManNAz and BYTES-Cu(I)-catalyzed click chemistry. (B, C, D) Flow cytometry data of cell surface labeling experiments described in (A) using LNCaP cells. (B) Cells were treated with biotin-azide or biotin-alkyne (100 µM) in the presence of the BTTESCu(I) catalyst ([Cu]=75 µM) for 1 or 2.5 min respectively before probing with streptavidin-Alexa Fluor 488 conjugates. In all cases, cells cultured in the absence of sugar displayed mean fluorescence intensity (MFI, arbitrary units) values <15. (C) Cells were labeled with biotin-azide (100 µM) for 1 min in the presence of 25-75 µM Cu(I). (D) Cells were labeled with biotinalkyne (100 µM) for 2.5 min in the presence of 25-75 µM Cu(I). Error bars represent the standard deviation of three replicate experiments. Solid line, +Ac$_4$ManNAl (C) or Ac$_4$ManNAz (D); dashed line, no sugar.
Figure 3A:
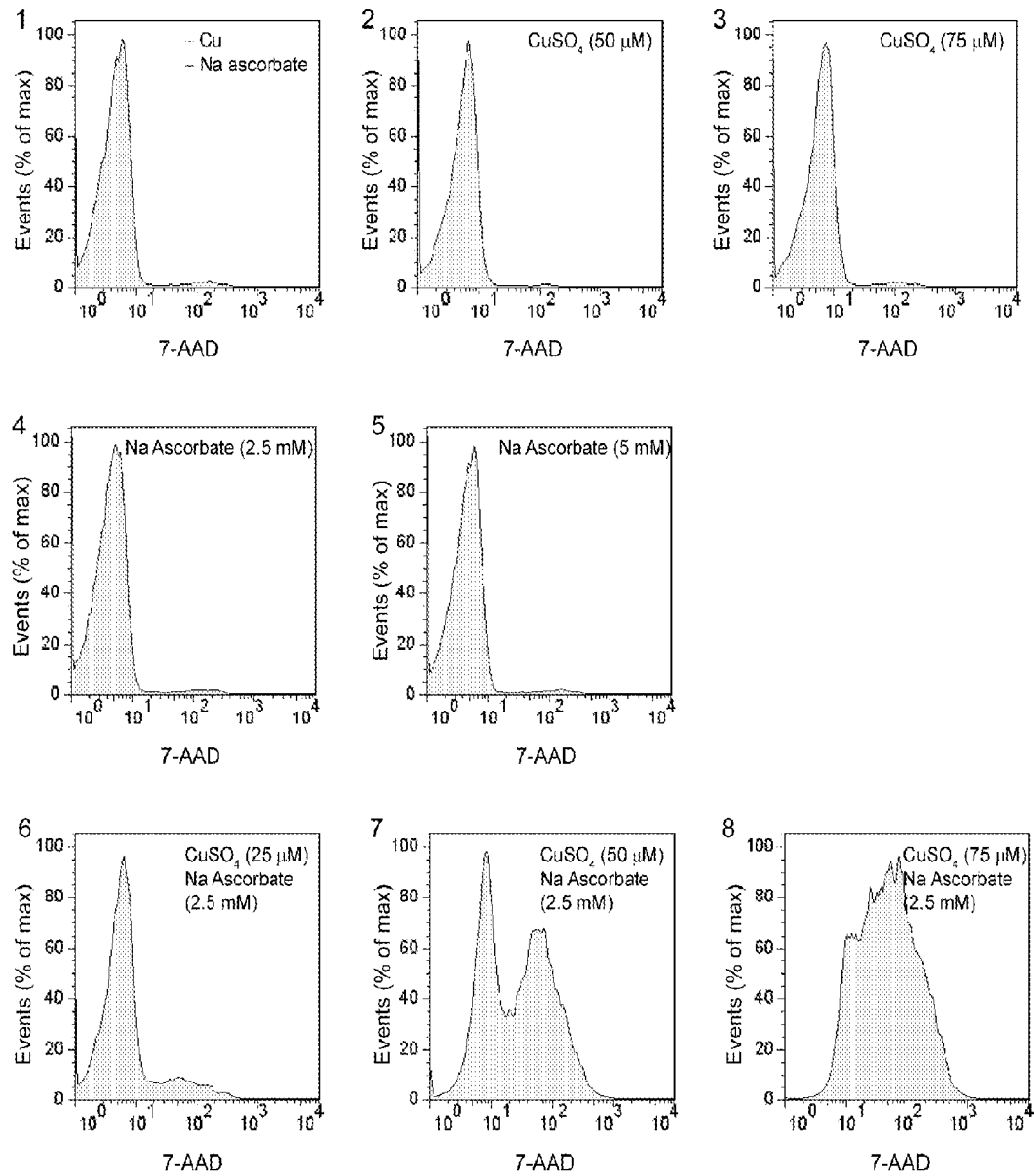
FIG. 3A-3B. Cytotoxicity analysis of CuAAC (Jurkat cells). Jurkat cells were cultured in medium supplemented with 50 μM (A) Ac$_4$ManNAl or (B) Ac4ManNAz (2 series). After 3 days, cells were incubated with CuSO$_4$ (2, 3) or Na ascorbate alone (4, 5) for 30 min or sodium ascorbate+ CuSO$_4$ in the absence (6-8, 12-14) or presence (9-11, 15-17) of BYTES for 5 min (ligand and CuSO$_4$ were premixed). Reactions were quenched with BCS. The cells were washed and diluted in FACS buffer supplemented with 2 μg/mL 7-AAD prior to flow cytometry analysis.
Figure 3B:
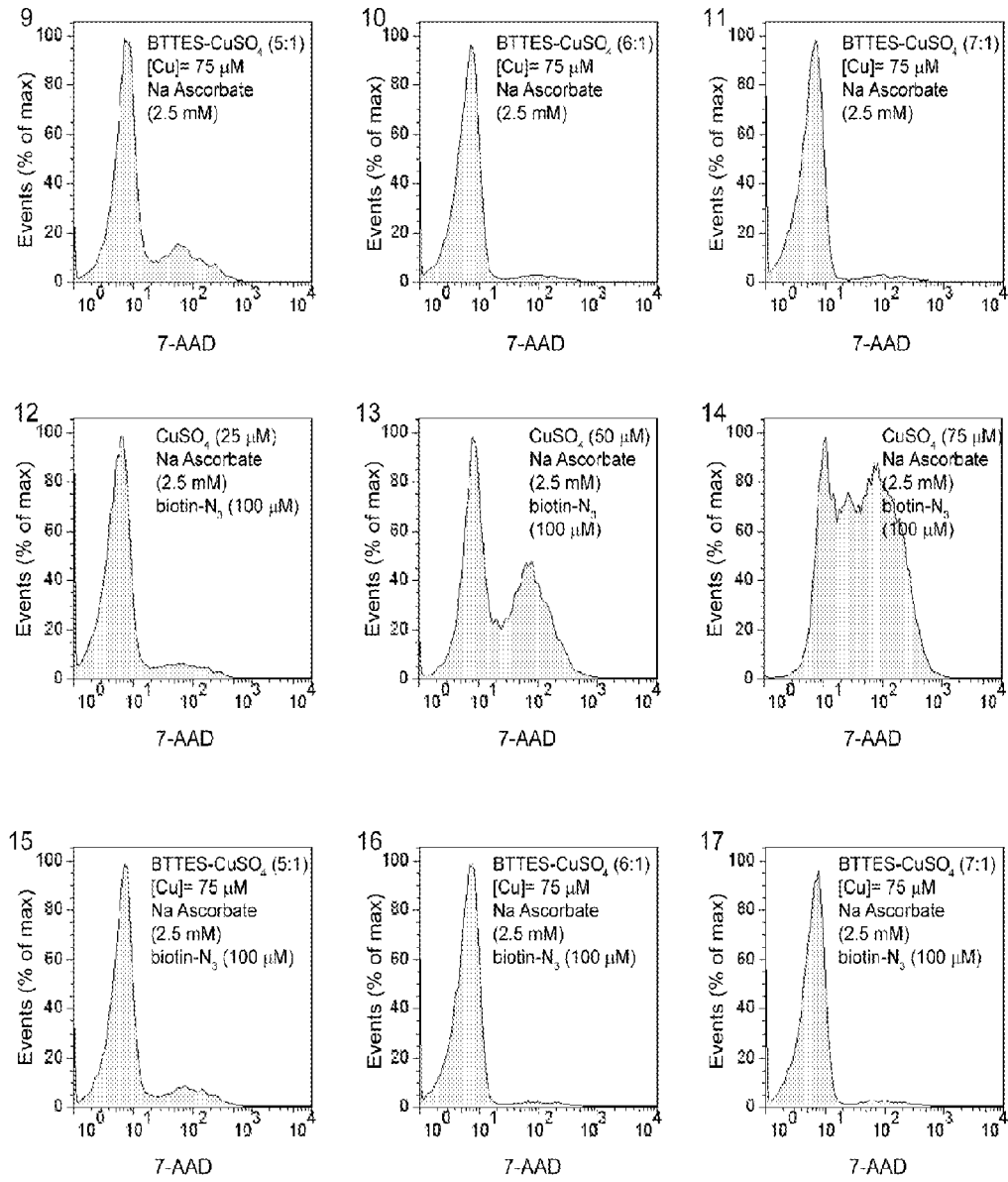
Figure 3C:
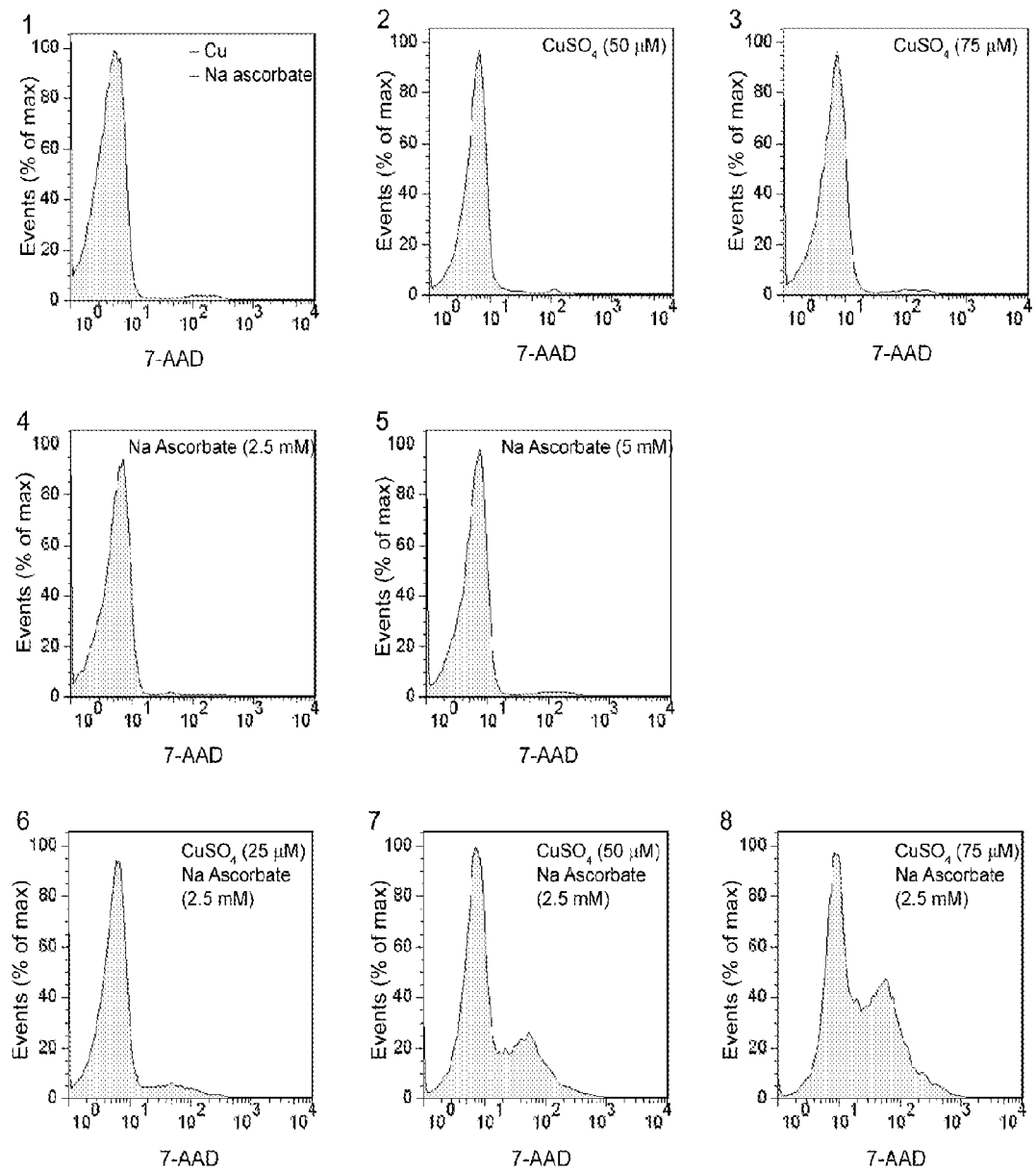
Figure 3D:
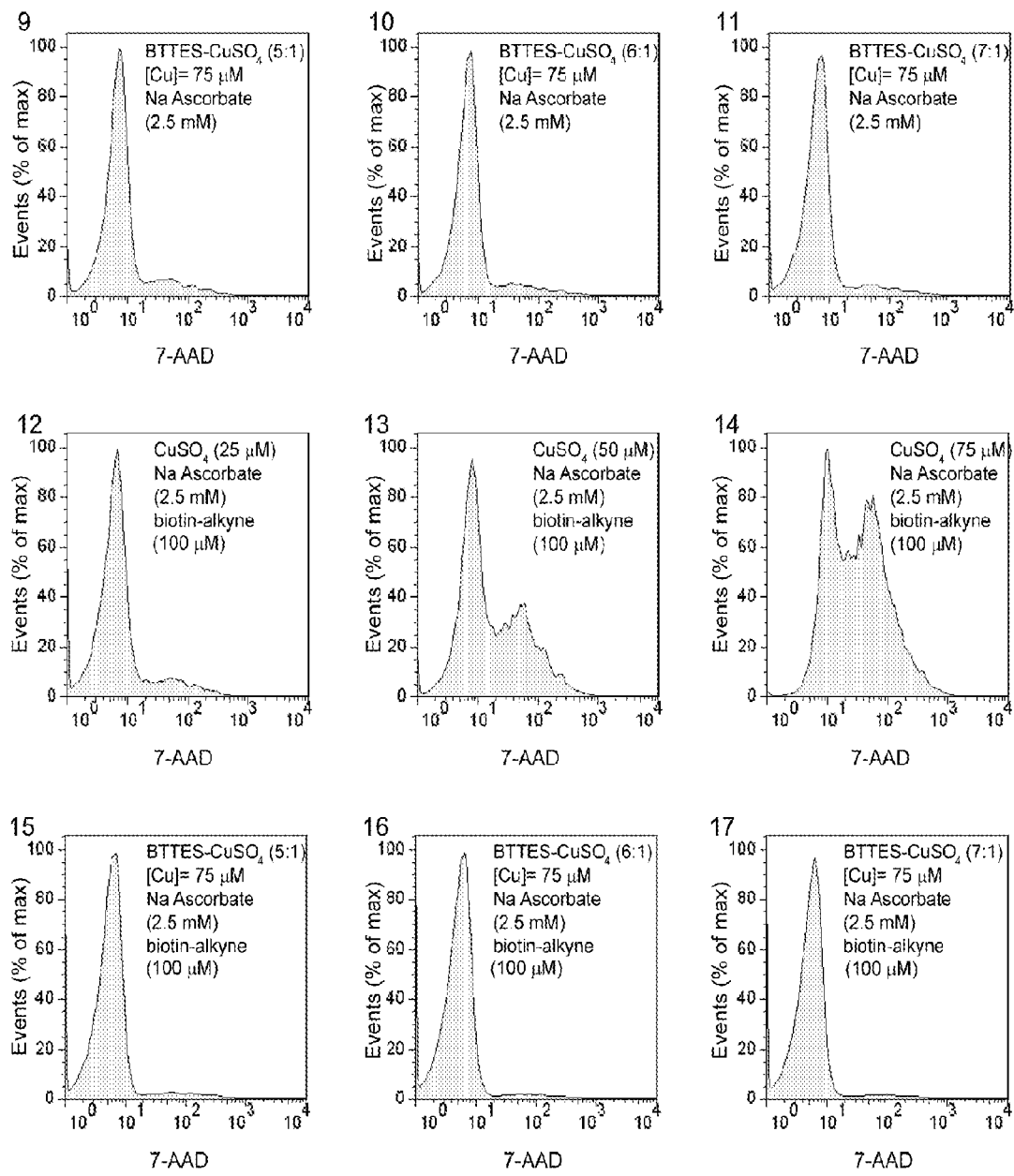
Figures 6A, 6B, 6C:
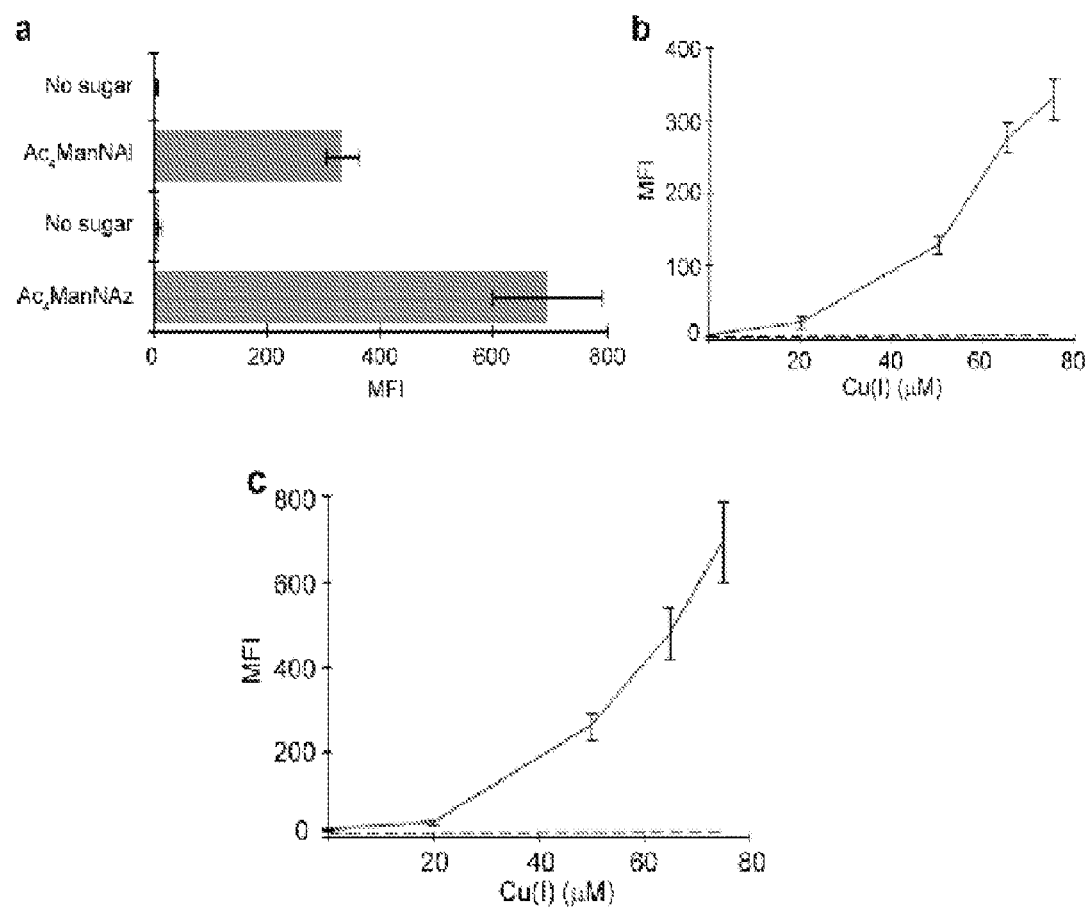
FIG. 6A-6C. Flow cytometry data of cell surface labeling experiments using HEK 293T cells. (A) Cells were treated with biotin-azide or biotin-alkyne (100 μM) in the presence of the BTTES-Cu(I) catalyst ([Cu]=75 μM) for 1 or 2.5 min respectively before probing with streptavidin-Alexa Fluor 488 conjugates. In all cases, cells cultured in the absence of sugar displayed mean fluorescence intensity (MFI, arbitrary units) values <15. (B) Cells were labeled with biotin-azide (100 μM) for 1 min in the presence of 25-75 μM Cu(I). (C) Cells were labelled with biotin-alkyne (100 μM) for 2.5 min in the presence of 25-75 μM Cu(I). Error bars represent the standard deviation of three replicate experiments. Solid line, +Ac$_4$ManNAl (B) or Ac$_4$ManNAz (C); dashed line, no sugar. When the SiaNAl-bearing HEK cells were treated with biotin-azide (100 μM) and the BTTES-Cu(I) catalyst ([Cu]=75 μM) for 90 s, the MFI is ~780.
Figures 7A, 7B, 7C:
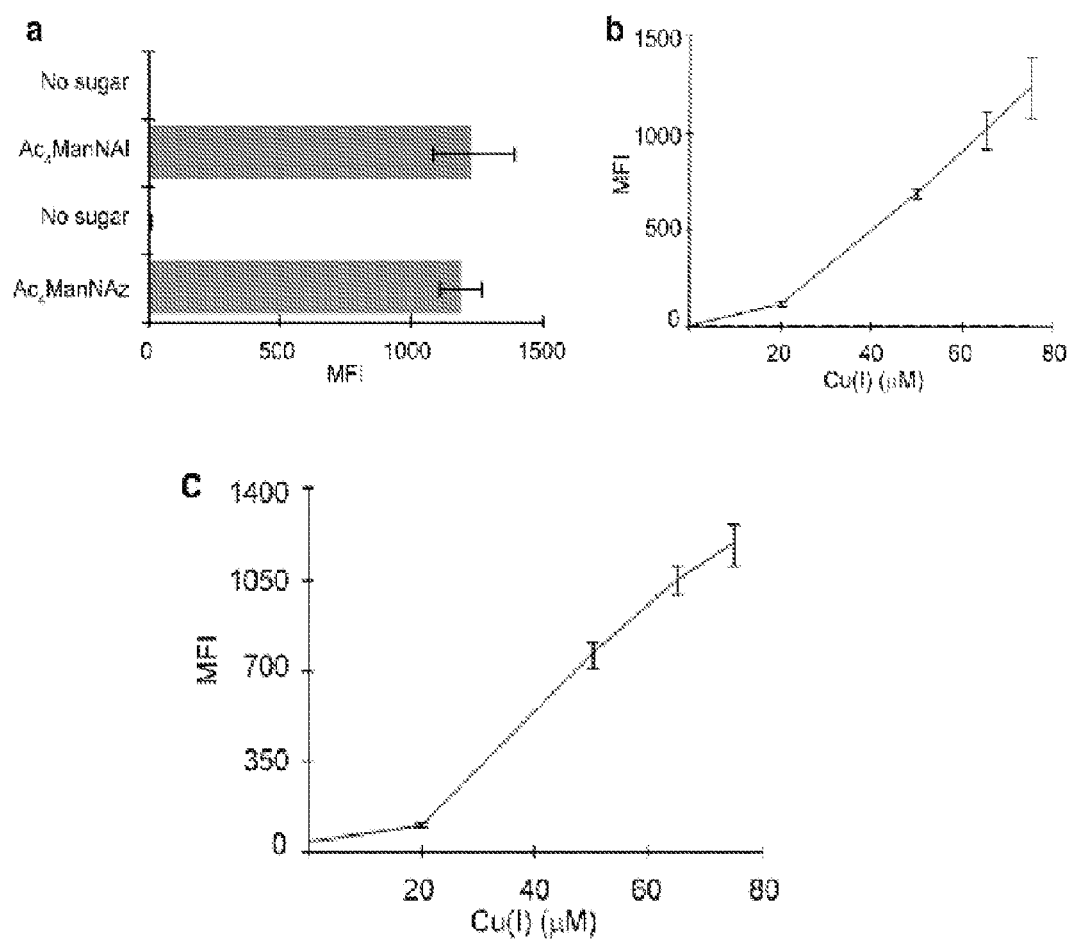
FIG. 7A-7C. Flow cytometry data of cell surface labeling experiments using Jurkat cells. (A) Cells were treated with biotin-azide or biotin-alkyne (100 μM) in the presence of the BTTES-Cu(I) catalyst ([Cu]=75 μM) for 1 or 2.5 min respectively before probing with streptavidin-Alexa Fluor 488 conjugates. In all cases, cells cultured in the absence of sugar displayed mean fluorescence intensity (MFI, arbitrary units) values <15. (B) Cells were labeled with biotin-azide (100 μM) for 1 min in the presence of 25-75 μM Cu(I). (C) Cells were labeled with biotin-alkyne (100 μM) for 2.5 min in the presence of 25-75 μM Cu(I). Error bars represent the standard deviation of three replicate experiments. Solid line, +Ac$_4$ManNAl (B) or Ac$_4$ManNAz (C); dashed line, no sugar. When the SiaNAl-bearing Jurkat cells were treated with biotin-azide (100 μM) and the BTTES-Cu(I) catalyst ([Cu]=75 μM) for 90 s, the MFI is ~5200.
Figures 8A, 8B, 8C:
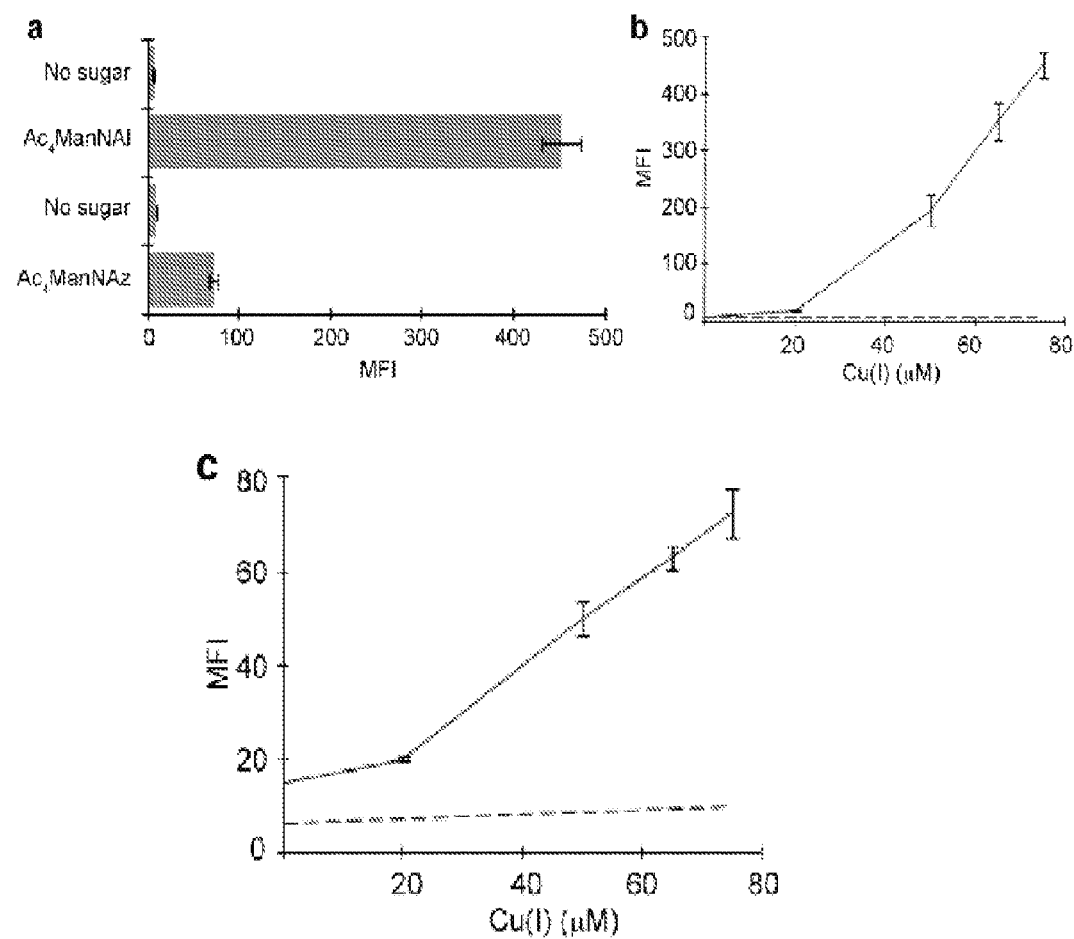
FIG. 8A-8C. Flow cytometry data of cell surface labeling experiments using Pro-5 CHO cells. (A) Cells were treated with biotin-azide or biotin-alkyne (100 μM) in the presence of the BTTES-Cu(I) catalyst ([Cu]=75 μM) for 1 or 2.5 min respectively before probing with streptavidin-Alexa Fluor 488 conjugates. In all cases, cells cultured in the absence of sugar displayed mean fluorescence intensity (MFI, arbitrary units) values <15. (B) Cells were labeled with biotin-azide (100 μM) for 1 min in the presence of 25-75 μM Cu(I). (C) Cells were labeled with biotin-alkyne (100 μM) for 2.5 min in the presence of 25-75 μM Cu(I). Error bars represent the standard deviation of three replicate experiments. Solid line, +Ac$_4$ManNAl (B) or Ac4ManNAz (C); dashed line, no sugar.

BTTES-Cu(I) Catalyzed Azide-Alkyne Cycloaddition Allows Rapid Detection of Sialylated Glycans on Live Cell Surface Next, the utility of the BTTES-Cu(I) catalyst for live cell labeling was investigated (the catalyst formulation: BTTES-CuSO$_4$ ([ligand]:[Cu]=6:1) complex and 2.5 mM sodium ascorbate). LNCaP cells, a human prostate adenocarcinoma cell line, bearing alkynyl (SiaNAl) or azido sialic acid (SiaNAz) residues within their cell-surface glycans were reacted with biotinazide or biotin-alkyne (100 µM) catalyzed by various concentrations of the copper catalyst for 1-2.5 min at rt and then stained with Alexa Fluor 488-streptavidin and analyzed by flow cytometry. Cells displaying alkyne or azide showed a dose-dependent increase in fluorescence upon treatment with the catalyst (FIGS. 2C and 2D). Cells lacking alkynyl or azido residues only showed background labeling (FIG. 2B). Similar results were observed for HEK 293T, a human embryonic kidney cell line, Jurkat and CHO cells (FIGS. 6, 7, 8). In all cell lines profiled, significantly higher fluorescence was detected in cells displaying alkyne on the cell surface than the corresponding azide-displaying counterparts, with robust labeling achieved within one min. This observation is consistent with the previous discovery that Ac$_4$ManNAl metabolism is more efficient than Ac$_4$ManNAz in these mammalian cell lines [22].

To measure the kinetics of the CuAAC on the cell surface, SiaNAz-expressing Pro-5 CHO cells were reacted with biotin-alkyne and the BTTES-Cu(I) catalyst ([Cu]=75 µM) for 2-17 min, followed by staining with Alexa Fluor 488-streptavidin. As quantified by flow cytometry analysis, the cell-associated Alexa Fluor 488 fluorescence reached a plateau around 14 min, indicating the completion of the ligation reaction between biotin-azide and the cell surface reagent-accessible SiaNAz. Importantly, during the 17-min course of the reaction, no cell apoptosis was observed.

Figure 9A:
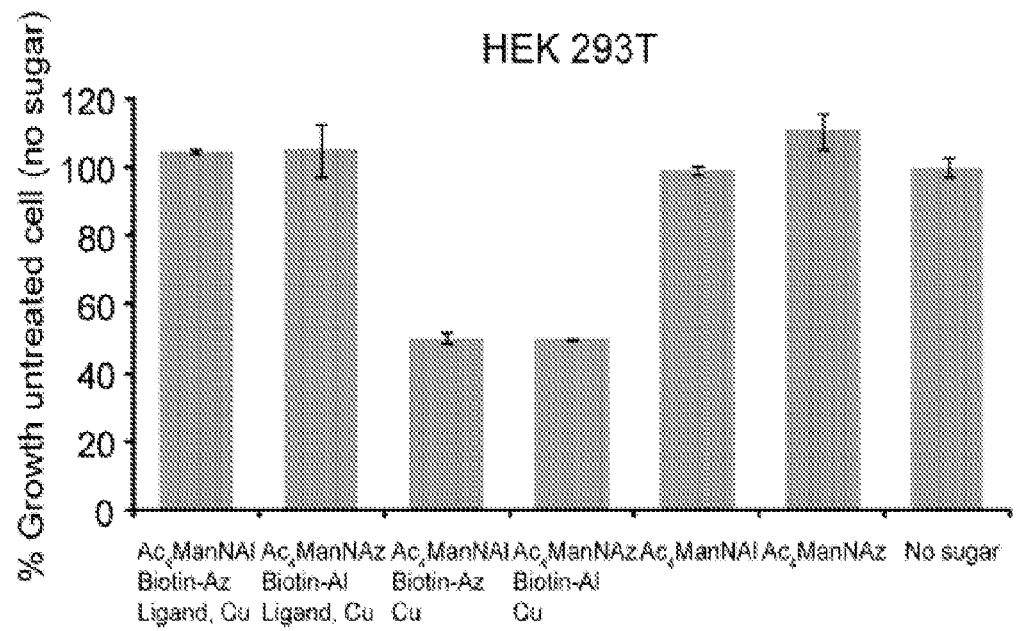
FIG. 9A-9B. BTTES-Cu(I)-catalyzed click chemistry has no long term perturbation to HEK293 (A) and Jurkat (B) cells. Cell viability measured using an alamarBlue assay (Invitrogen). Error bars: standard derivation for three replicates.
Figure 9B:
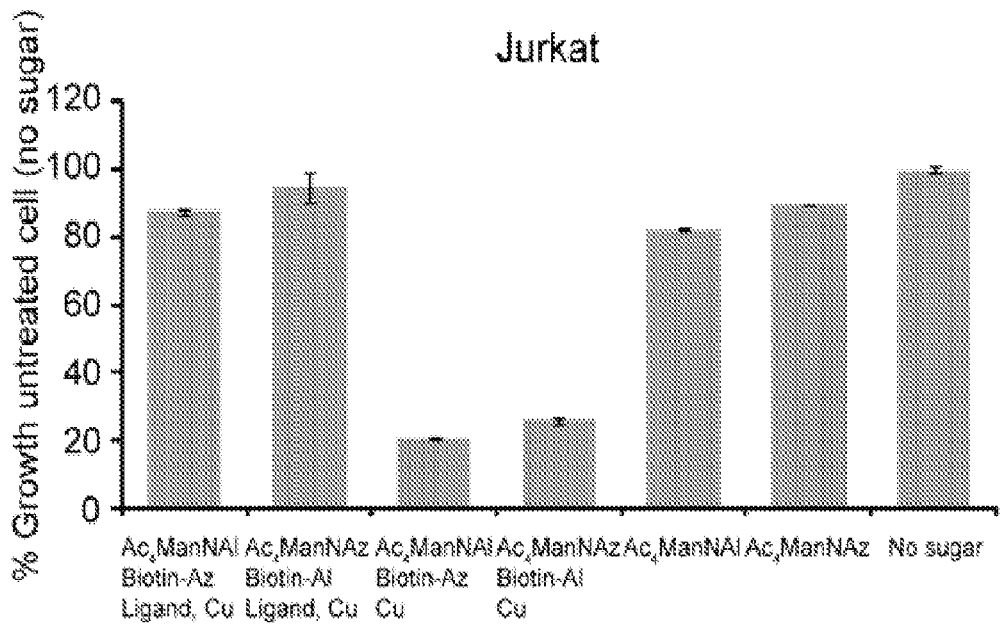

To evaluate if BTTES-Cu(I)-catalyzed click chemistry causes any long term perturbation to the treated cells, Jurkat and HEK 293T cells bearing SiaNAz or SiaNAl residues were labeled with biotin-azide or biotin-alkyne in the presence of the catalyst ([Cu]=75 µM) for 3 min. The reactions were then quenched with BCS. The catalyst-treated cells were cultured for three to four days. In control experiments, cultures were made of untreated cells and cells treated with in situ generated Cu(I) in the absence of ligand. Viable cells, based on Trypan Blue assay, were counted each day. Cells treated with the BTTES-Cu(I) catalyst proliferated at similar rates as untreated cells. By contrast, all cells labeled in the absence of BTTES underwent lysis within 24 h of the labeling experiments. Similar results were obtained using an alamarBlue cell viability assay (FIG. 9). Taken together, the discovery of BTTES creates a nontoxic and highly efficient Cu(I) catalyst for azide-alkyne cycloaddition, setting the stage to test its use for in vivo imaging of azide- and alkyne-tagged biomolecules.

Metabolic Labeling with Ac$_4$ManNAz Allows Imaging of Sialylated Glycans in Developing Zebrafish The development of a multicellular organism as it grows from a single zygote to a complex system of tissues is accompanied by complex changes of glycosylation on the cell surface. To test if the biocompatible copper catalyst could be extended to image the dynamic changes of glycans in vivo, the rapid embryonic development and optical clarity of the zebrafish embryo was taken advantage of as a vertebrate model system.

The first class of glycans chosen to explore in developing zebrafish was sialylated glycans. Sialic acids, a family of monosaccharides widely expressed as a terminal modification of both N- and O-linked glycans, are known to perform numerous functions during zebrafish development. For example, linear homopolymers of sialic acids, known as polysialic acid, are key mediators of axon growth and pathfinding during zebrafish central nervous system development [30]. Moreover, sialylated glycans also contribute to tissue segmentation and somite formation of the zebrafish embryo [31]. As discussed previously, the sialic acid biosynthetic pathway can be hijacked by treating cells or organisms with an azide-derivatized precursor, Ac$_4$ManNAz. Ac$_4$ManNAz, taken up by the developing embryos, is enzymatically deacetylated and enters the metabolic pathway for conversion to an azide-bearing CMP-sialic acid (CMPSiaNAz), the universal sialyl donor. Sialyltransferases, 18 of which have been identified in the zebrafish [32, 33], transfer SiaNAz to acceptor glycans. The embryos were bathed in medium supplemented with Ac$_4$ManNAz (5 mM) following the protocol developed by Bertozzi [21]. 24 h later, the embryos were reacted with Alexa Fluor 488-alkyne (488-alkyne) in embryo medium (100 µM) with the BTTES-Cu(I) catalyst ([Cu]=65 µM) to detect azide-tagged sialic acids. Immediately following a 5-min reaction, a marked increase in fluorescence in these embryos compared to embryos treated with Ac$_4$ManNAc was observed. After the reaction, development of the labeled embryos were followed for three days, and no developmental defects were observed as compared to their untreated counterparts, suggesting that the Cu(I)-catalyst was well tolerated by the zebrafish embryos.

Microinjection of FucAl Allows Imaging of Fucosylated Glycans During the Late Gastrulation and Tissue Segmentation Periods of Zebrafish Embryogenesis Similar to sialylation, specific terminal glycan fucosylation can confer unique properties to cell surface glycoconjugates and are often regulated in cellular differentiation and embryogenesis [34]. There is evidence that Lewis X (Le$^x$), an α1,3 fucosylated trisaccharide, serves as a biomarker for murine pluripotent stem cells, in which it plays an important role in adhesion, guiding the migration of cells in the preimplantation embryo [34, 35]. Studies have also shown that during development of the zebrafish nervous system, neuroepithelial cells require fucosylated glycans to guide the migration of vagus motor neuron progenitors in the developing hindbrain [36]. Despite the physiological significance of these fucosylated glycans, there is currently no method for imaging them in live cells or organisms [37, 38].

Fucosylated glycans in zebrafish embryos by exploiting the fucose salvage pathway to incorporate terminal alkyne-bearing analogues into cell surface glycoproteins and glycolipids [38, 39]. This pathway begins with the uptake of free fucose, which is converted into fucose-1-phosphate by fucokinase, and thence to GDP-fucose by GDP-fucose pyrophosphorylase (FIG. 4A) [40]. GDP-fucose serves as the substrate for fucosyltransferases, which transfer the fucose residue to acceptor glycans within the secretory pathway. The modified glycoconjugates are then delivered to the cell surface or secreted. Wong and coworkers discovered that FucAl (FIG. 4A), a 5-alkyne-modified fucose analogue, is well tolerated in the salvage pathway of several mammalian cell lines [38].

Figures 4A, 4B, 4C, 4D, 4E:
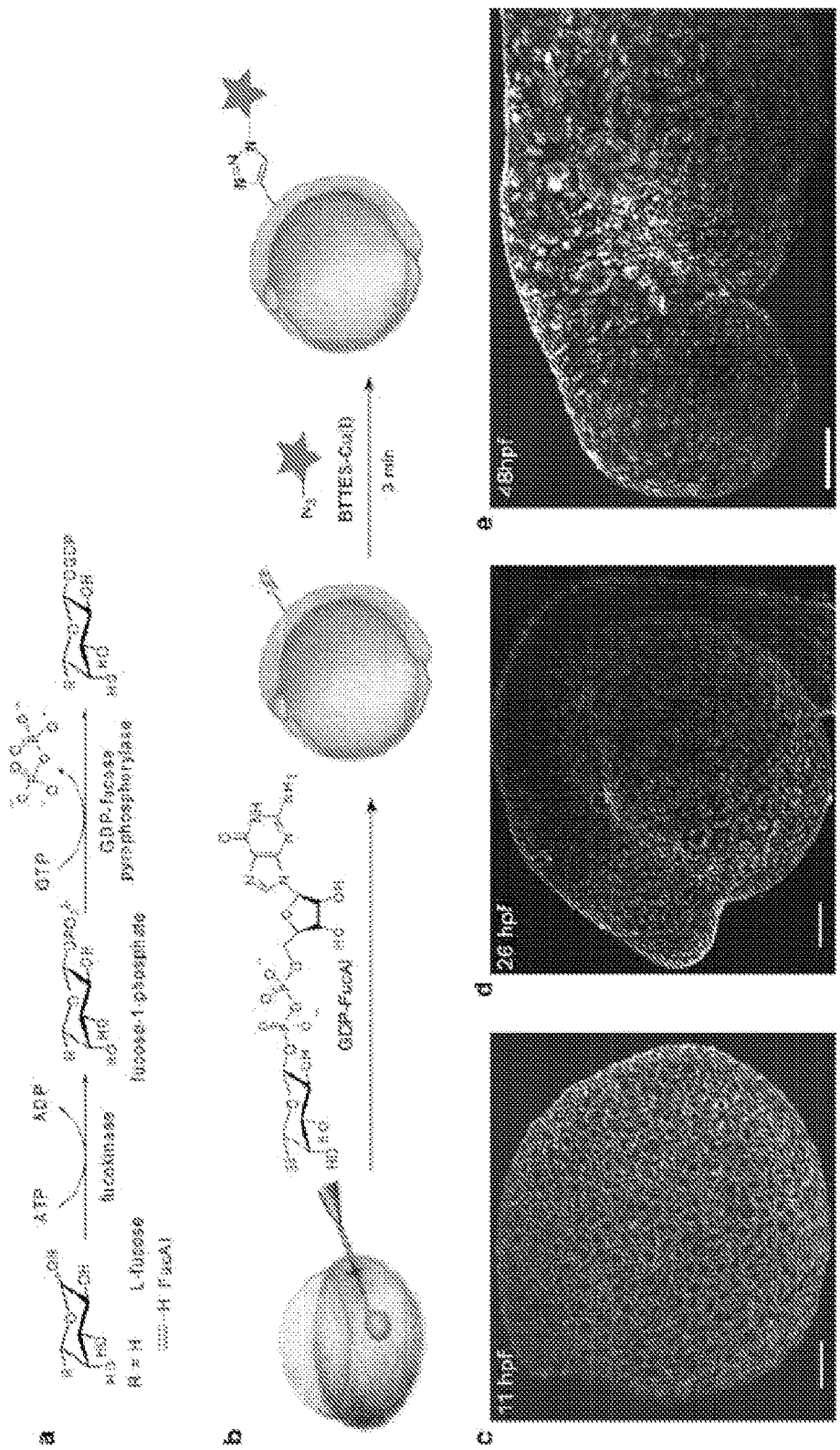
FIG. 4A-4E. In vivo imaging of fucosylated glycans during early zebrafish embryogenesis via BTTES-Cu(I)-catalyzed click chemistry. (A) FucAl is a substrate of the GDP-fucose salvage pathway. (B) Microinjection combined with the BYTES-Cu(I)-catalyzed click chemistry enables the labeling of fucosylated glycans. Zebrafish embryos were microinjected with a single dose of GDP-FucAl and allowed to develop to 11 hpf (C), 26 hpf (D) and 48 hpf (E). The embryos were then reacted with 488-azide catalyzed by BYTES-Cu(I) and imaged using confocal microscopy. z-projection fluorescence images shown in (C) were acquired at 11 hpf Scale bar: 100 μm.
Figures 10A, 10B:
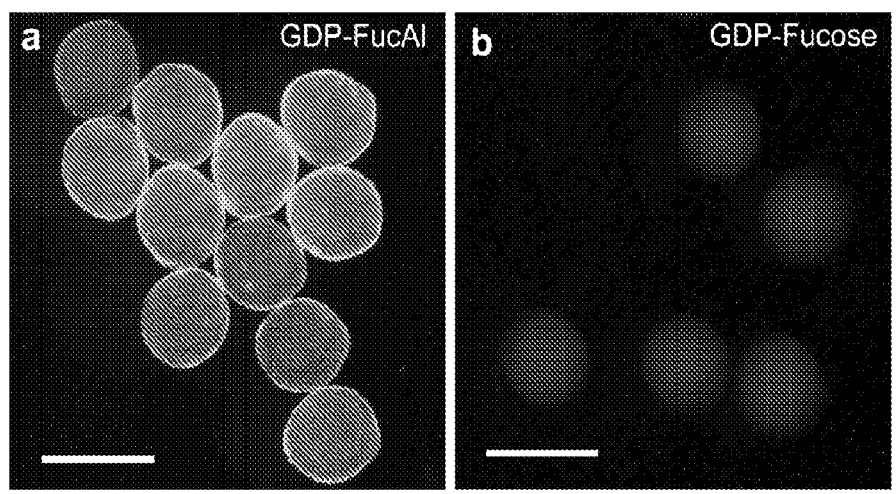
FIG. 10A-10B. In vivo imaging of fucosylated glycans during early zebrafish embryogenesis via BTTES-Cu(I)-catalyzed click chemistry. One-cell embryos microinjected with a single dose of GDP-FucAl (A) or GDP-fucose (B) were allowed to develop to 10 hpf. The embryos were then reacted with 488-azide catalyzed by BTTES-Cu(I) and imaged using fluorescence microscopy. Scale bar: 1 mm.

To image fucosylated glycans in zebrafish embryos, GDP-FucAl was synthesized chemoenzymatically [39] and microinjected embryos at the one-cell stage with 20 pmol of GDP-FucAl (FIG. 4B). The embryo was dechorionated and reacted at 10 hpf with 488-azide in the presence of the BTTES-Cu(I) or BTTA-Cu(I) catalyst ([Cu]=50 µM). Robust labeling of the treated embryos was achieved within 1-3 min reaction (FIG. 4C), and only background fluorescence was detected for control embryos microinjected with GDP-fucose (FIG. 10). Embryos were also reacted at 6.5 hpf and achieved strong labeling of fucosides after a 3-min click reaction. To examine the developmental period during which a single dose of GDP-FucAl could yield a detectable alkyne-dependent fluorescent signal, the labeling timecourse was extended to 48 hpf, at which point the zebrafish is already a bilaterally organized creature in the pharyngula period. After labeling with Alexa Fluor 488-azide, robust labeling was observed for embryos at the early (26 hpf) and late (48 hpf) pharyngula stages (FIG. 4D, 4E), which are distinguishable by progressive development of the pectoral fins, the median fin fold, and the pigmentation pattern produced by the melanophores. As revealed by individual z-planes obtained using confocal fluorescence microscopy, only the enveloping layer of the blastodisc was labeled by the Alexa fluorophore due to the low tissue penetration depth of the click chemistry reagents.

Dynamic Multicolor Imaging of Fucosylated Glycans in Zebrafish Embryos

Figures 5A, 5B, 5C:
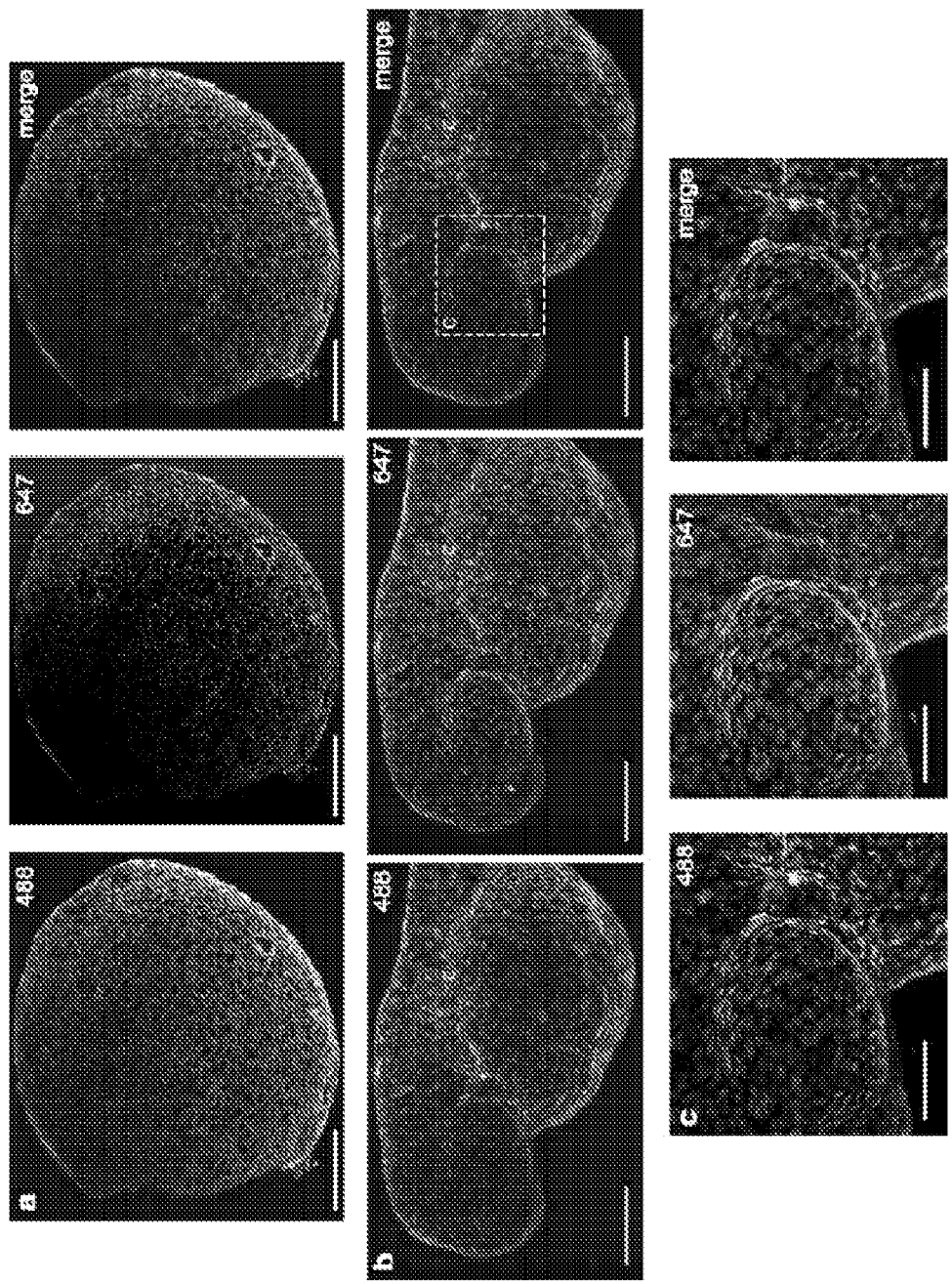
FIG. 5A-5C. Imaging of fucosylated glycans during early zebrafish development. One-cell embryos were microinjected with a single dose of GDP-FucAl and allowed to develop to 10 hpf (A) and 30 hpf (B). The embryos were reacted with 488-azide catalyzed by BTTES-Cu(I). The younger and older embryos were allowed to develop for another hour or 24 h, respectively, followed by a second click reaction with 647-azide, and imaged using confocal microscopy. (A) z-projection fluorescence image of an 11-hpf embryo. (B) z-projection fluorescence image of a 54-hpf zebrafish (lateral view). (C) z-projection fluorescence images of the eye region highlighted in (B). Scale bar: 200 μm.

The biocompatible nature of the BTTES-Cu(I)-catalyzed click chemistry allowed performance of time-lapse imaging experiments to monitor the trafficking of the alkyne-tagged fucosides in developing zebrafish embryos. Toward this goal, embryos were microinjected at the one-cell stage with GDP-FucAl. At the onset of the tail bud stage (10 hpf) or in the middle of the pharyngula period (30 hpf), embryos were treated with 488-azide in a click reaction catalyzed by the BTTES-Cu(I) for 3 min. After the reaction was quenched with BCS, the younger embryos were allowed to develop for an additional 1 h and the older ones were allowed to develop for another 24 h, respectively. A second click reaction was then performed with 647-azide to label the newly synthesized fucosides on the enveloping layer of the embryos. As shown in FIG. 5A-5C, the dynamic addition of fucosides during the segmentation and pharyngula stages of embryogenesis could be captured.

The first reaction conducted at ten hours of development, revealed abundant cell-surface fucosylation as evident from the robust labeling with 488-azide (FIG. 5A, left). The second labeling with 647-azide, conducted 1 h later at the onset of tissue segmentation, was weaker, an expected result given the short lag between the two intervals (FIG. 5A, middle). Nonetheless, incomplete overlap between the populations of glycans labeled at the two time points indicated that new sugars were added to the surface during the one-hour period between the two labeling reactions. During the pharyngula and hatching periods, abundant fucosylated glycans were produced as revealed by the robust labeling observed at the 30 hpf (FIG. 5B, left) and at the 54 hpf time points (FIG. 5B, middle). Incomplete overlap between these two labeled glycan populations indicated that new fucosides were added over this developmental window. Moreover, in certain regions of the embryo, in particular the developing eye and pectoral fin regions, the 647-azide labeling was more robust than the earlier 488-azide labeling, possibly reflecting locally elevated de novo synthesis and trafficking of fucosides as these structures develop (FIG. 5C). Notably, no apparent morphological changes or developmental defects were observed for the embryos treated with the sequential click reactions.

TABLE 1

Structure of the library of TBTA analogues screened

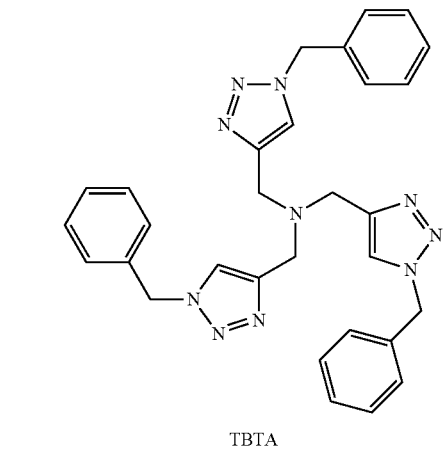 [SMILES: c1ccc(Cn2cc(CN(Cc3cn(Cc4ccccc4)nn3)Cc3cn(Cc4ccccc4)nn3)nn2)cc1 ; "TBTA"]

(1) TBTA

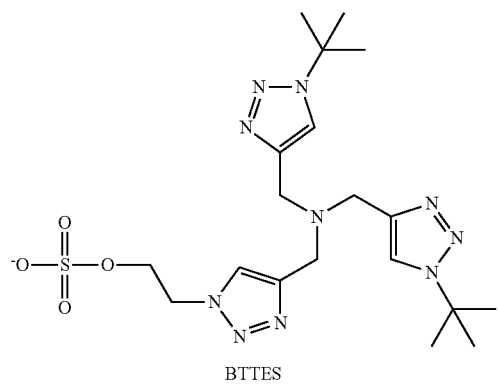

(2) BTTES

TABLE 1-continued

Structure of the library of TBTA analogues screened

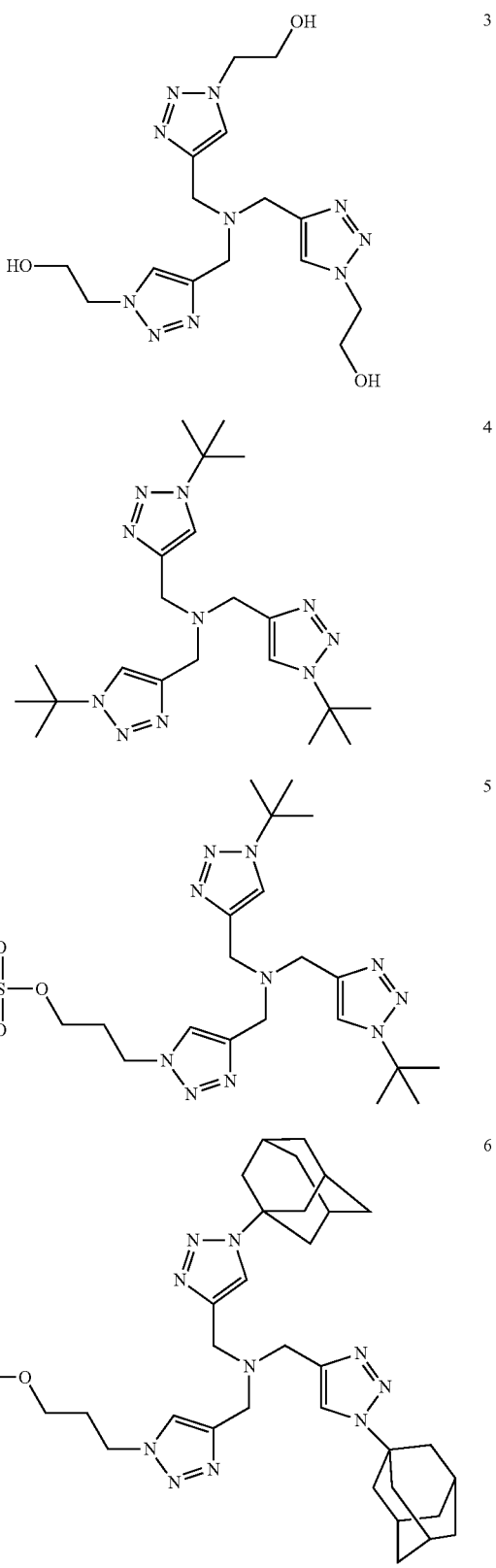

TABLE 1-continued
Structure of the library of TBTA analogues screened
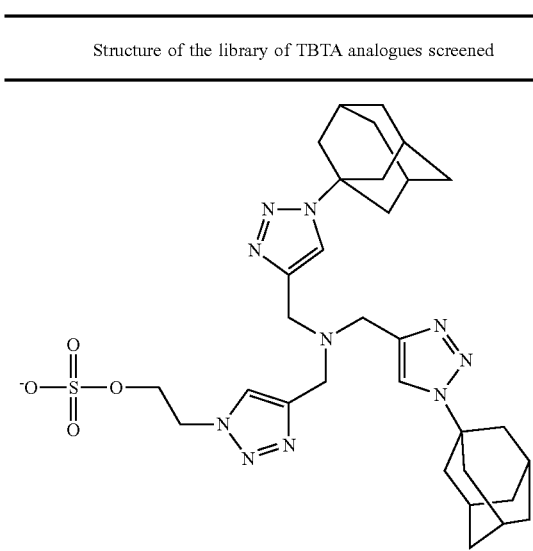
7
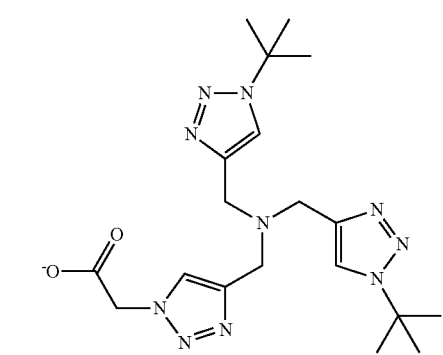 [SMILES: CC(C)(C)n1cc(CN(Cc2cn(CC(=O)[O-])nn2)Cc2cn(C(C)(C)C)nn2)nn1]
8
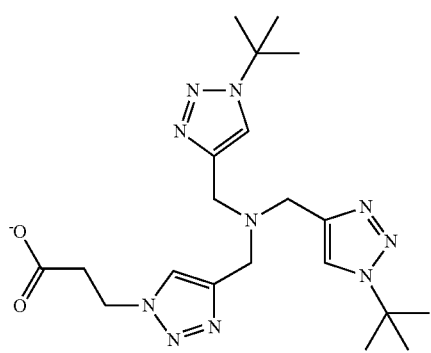 [SMILES: CC(C)(C)n1cc(CN(Cc2cn(CCC(=O)[O-])nn2)Cc2cn(C(C)(C)C)nn2)nn1]
9
TABLE 1-continued
Structure of the library of TBTA analogues screened
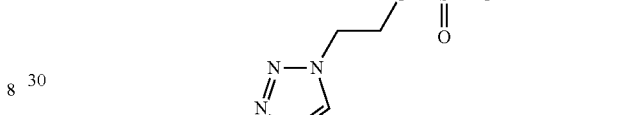
10
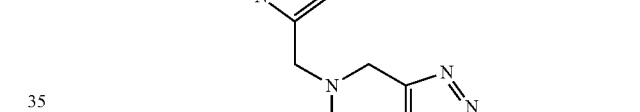
11
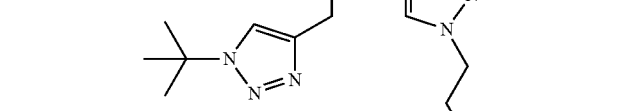
12

TABLE 1-continued

Structure of the library of TBTA analogues screened

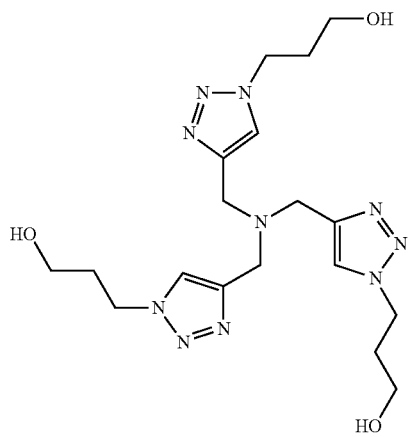 [SMILES: OCCCn1cc(CN(Cc2cn(CCCO)nn2)Cc2cn(CCCO)nn2)nn1]

13

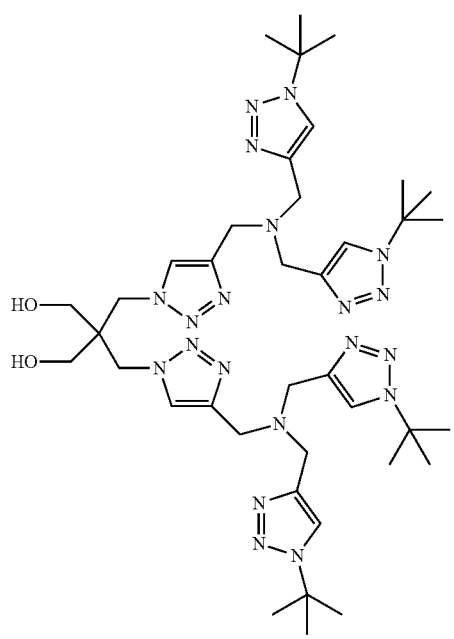 [SMILES: CC(C)(C)n1cc(CN(Cc2cn(CC(CO)(CO)Cn3cc(CN(Cc4cn(C(C)(C)C)nn4)Cc4cn(C(C)(C)C)nn4)nn3)nn2)Cc2cn(C(C)(C)C)nn2)nn1]

14

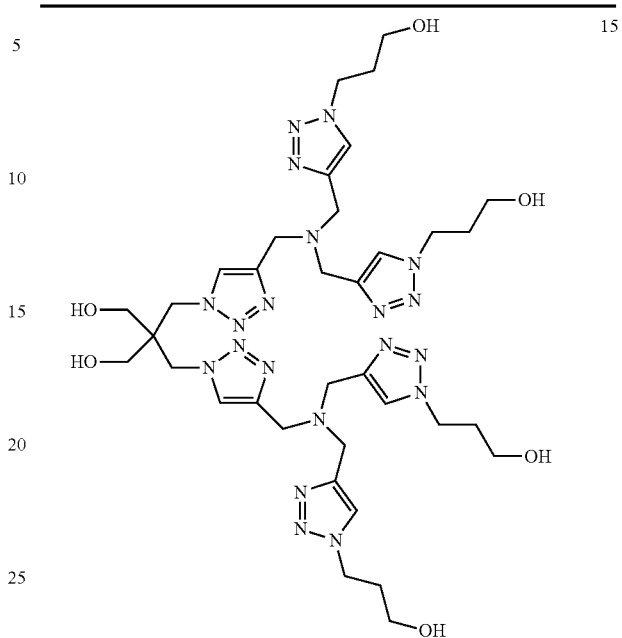

15

3. Discussion

Imaging the glycome within a cellular environment is now possible using new tools from the emerging field of bioorthogonal click chemistry [43]. With the discovery of the tris(triazolylmethyl)amine-based ligand BTTES, a practical and biocompatible click reaction has been identified that allows the analysis of dynamic glycan biosynthesis during zebrafish early development. Robust labeling, which requires 1 h of reaction time when using the cyclooctyne-based copper-free click chemistry, was achieved within minutes. Little toxicity or developmental abnormalities resulting from treatments with the Cu(I) catalyst were observed through four days post click reaction. Among the 120 embryos microinjected with various nucleotide sugar analogues and treated with the click reagents, less than twelve embryos exhibited minor developmental defects, i.e. impaired posterior body development characterized by a shorter anterior-posterior axis. Comparable phenotypes were observed in 10% of embryos that were injected but were not treated with the click reagents (n ~1000), suggesting that the defects may be due to microinjection rather than the click reaction.

The BTTES-Cu(I) catalyst, combined with yolk-cell microinjection, allows for the first time rapid imaging of fucosylated glycans in the enveloping layer of zebrafish embryos as early as ten hours post fertilization. Since transplantation can be easily performed from labeled donor embryos to unlabeled hosts beginning with blastula stages (4 hpf) through the onset of gastrulation (5.3 hpf), exploiting this manipulation may allow us to follow the allocation of these glycans in specific lineages of the embryo during development.

Importantly, this work represents the first study of glycan biosynthesis during early zebrafish embryogenesis and adds the alkynyl functionality to the bioorthogonal reagent repertoire of in vivo imaging. As the synthesis of BTTES and BTTA can be easily scaled up to multigrams and many azide- and alkyne-functionalized reagents are commercially available, only genetic or metabolic manipulations are required to generate the tagged biomolecules in vivo for this new procedure of click modification. Thus, the chemical tools reported here can be directly applied for studying other sectors of the glycome and be generalized for dynamic in vivo imaging or profiling of other biomolecules, i.e. proteins, lipids and cofactors, many of which are already targets of the canonical click chemistry in vitro [12].

Example II

Labeling of Live Mammalian Cells

Figures 12A, 12B, 12C, 12D:
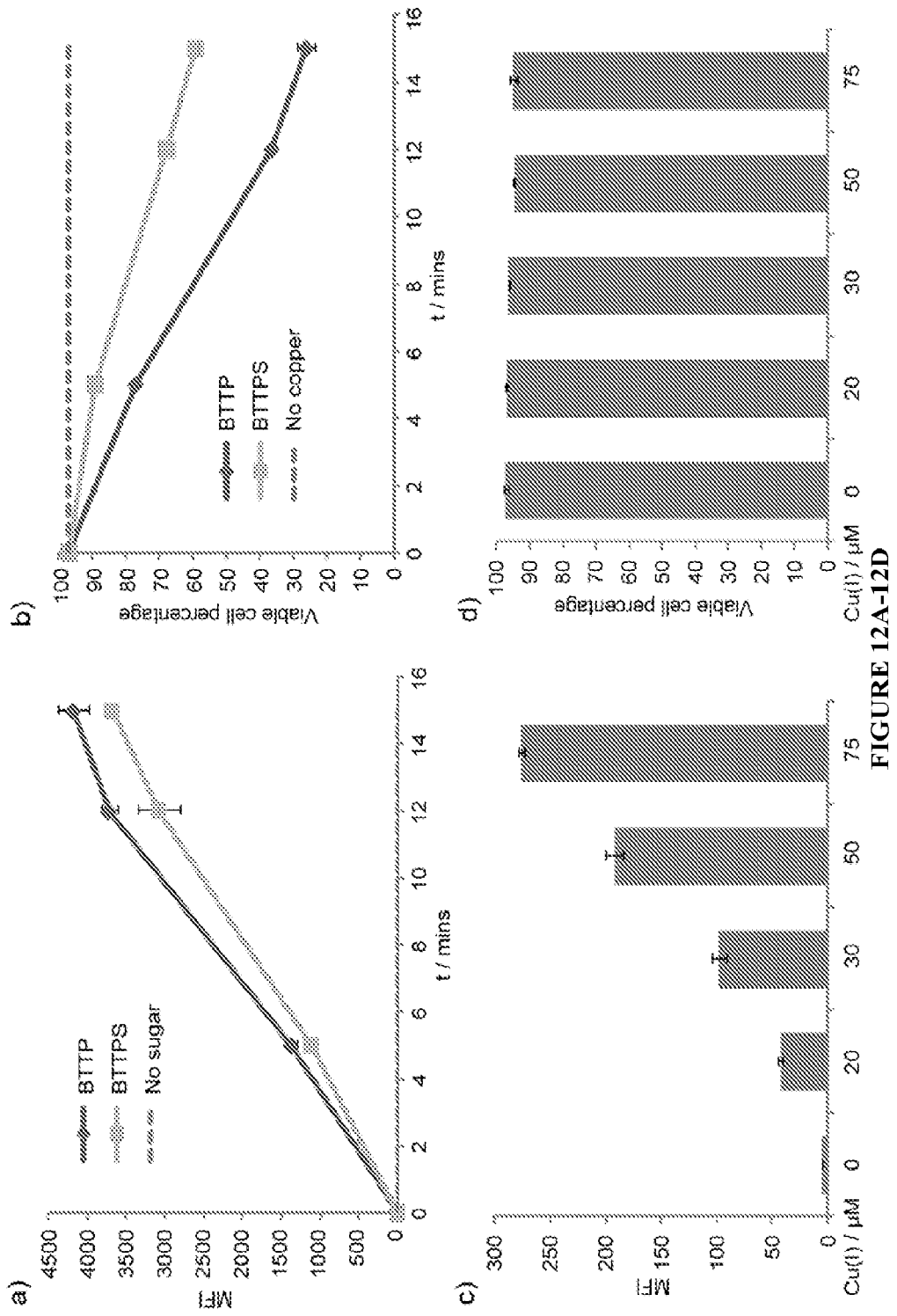
FIG. 12A-12D. Comparison of the efficiency of the BTTPS-Cu(I) and BTTP-Cu(I)-mediated azide-alkyne cycloaddition in labeling sialylated glycoconjugates in live cells. Jurkat cells were cultured in the presence or absence of Ac$_4$ManNAl for 3 days. Cells were then reacted with biotin azide (50 μM) in the presence of sodium ascorbate (2.5 mM), and CuSO$_4$ premixed with ligands BTTPS or BTTP ([ligand]:[CuSO$_4$]=6:1). Reactions were quenched with BCS, stained with Alexa Fluor 488-streptavidin, 7-AAD, and analyzed by flow cytometry. (A) Mean fluorescence intensity (MFI) of cells treated with the BTTPS-Cu(I) or BTTP-Cu(I) catalyst ([CuSO$_4$]=75 μM) in the course of 5-15 min reactions. (B) Percentage of viable cells without cell-membrane damage post the click reactions with the BTTPS-Cu(I) or BTTP-Cu(I) catalyst ([CuSO$_4$]=75 μM) in the course of 5-15 min reactions. (C) MFI of cells treated with the BTTPS-Cu(I) catalyst ([CuSO$_4$]=20-75 μM) in a one-minute reaction. (D) Percentage of viable cells without cell-membrane damage post the click reactions with the BTTPS-Cu(I) catalyst ([Cu]=20-75 μM) in a one-minute reaction.
Figure 14:
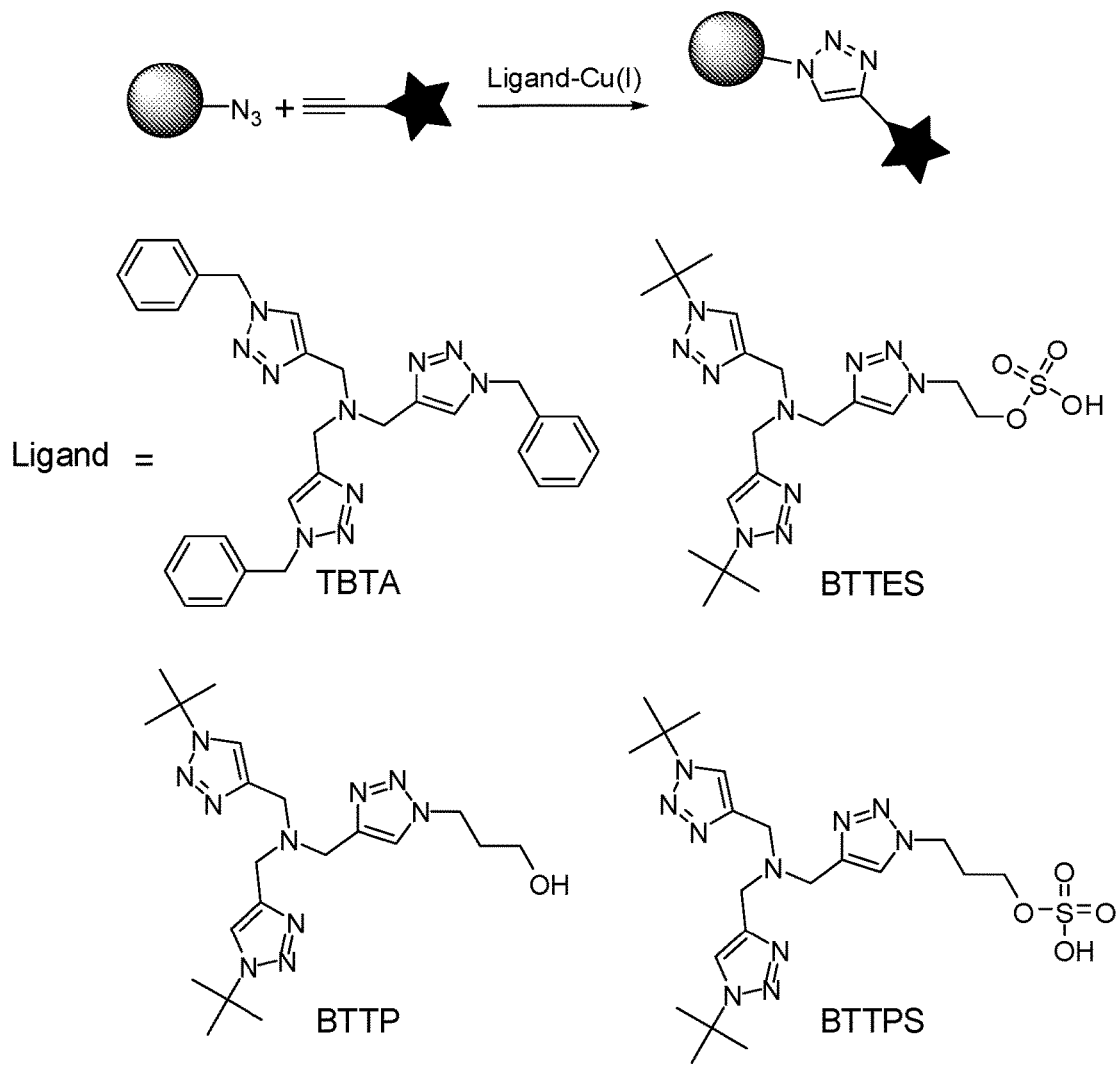
FIG. 14. Sulfation of ligands, TBTA and BTTP.

In the ligand design, sulfation of BTTP is used to generate a negatively charged ligand, BTTPS (3-(4-((bis((1-tert-butyl-1H-1,2,3-triazol-4-yl)methyl)amino)methyl)-1H-1,2,3-triazol-1-yl)propyl hydrogen sulfate), (FIG. 14) to minimize the cellular internalization of the coordinated copper. To evaluate if sulfation confers the ligand the desired property, BTTPS-Cu(I) and BTTP-Cu(I) were compared in live cell labeling experiments. Jurkat cells were metabolically labeled with $Ac_4ManNAl$. The treated cells were reacted with biotin-azide (50 µM) in the presence of BTTPS-Cu(I) or BTTP-Cu(I) for 5-15 min at room temperature (catalyst formulation: [ligand]:[$CuSO_4$]=6:1, [$CuSO_4$]=75 µM). After the reaction was quenched with BCS, the biotinylated cells were incubated with Alexa Fluor 488-streptavidin. The cells were then stained with 7-aminoactinomycin D (7-AAD), a fluorescent molecule with strong affinity for double-stranded DNA, and analyzed by flow cytometry. 7-AAD does not pass through intact membrane, but it readily enters damaged cells with compromised membrane. Therefore, healthy and damaged cells can be easily distinguished. As shown in FIG. 12a, cell-associated Alexa Fluor 488 fluorescence was detected for both BTTPS-Cu(I) or BTTP-Cu(I) treated cells, and the fluorescence increased along with the increase of the reaction time. Although both catalytic systems showed comparable labeling efficiency, BTTPS-Cu(I) was significantly better in protecting cells from the Cu(I)-associated toxicity, especially for labeling with extended reaction course (15 minutes). Greater than 60% cells were still undamaged after treatment with BTTPS-Cu(I) (7-AAD negative), whereas only 26% cells treated with BTTP-Cu(I) reminded normal (FIG. 12b). Furthermore, the labeling temperature also plays a significant role in modulating the Cu-associated toxicity. When both Jurkat cells and the labeling reagents were pre-cooled to 4° C. before triggering the CuAAC, greater than 85% cells remained viable after a 15 min BTTPS-Cu(I)-mediated reaction with high labeling efficiency achieved (mean fluorescence intensity 2200, for reactions performed at 4° C.-room temperature vs 3679, for reactions performed at room temperature).

To evaluate the activity of the new ligand-Cu(I) complex and compare the click reactions in the context of biomolecular labeling experiments, the first system used was a recombinant glycoprotein—Programmed Death 1-Immunoglobulin G Fc fusion (PD1-Fc). When expressed in mammalian cells, the Fc region of the recombinant protein is glycosylated and terminated with sialic acids. HEK-293 cells stably expressing PD1-Fc fusion protein were cultured in medium containing 50 µM sialic acid metabolic precursor—peracetylated N-azidoacetylmannosamine ($Ac_4ManNAz$) for 4 days. The target protein was then isolated using protein G (a genetically engineered protein that contains Fc binding domains of protein G) agarose. To probe for the presence of the sialic acid-associated azide, the protein was reacted with biotin-alkyne via the CuAAC or BARAC-biotin via the copper-free click chemistry. For the CuAAC, 100 µM of biotin-alkyne was used as the coupling partner and the ratio of biotin-alkyne, ligand, $CuSO_4$ and sodium ascorbate was held at 1:5:2.5:25, a labeling condition optimized in the lab. The copper-free click chemistry was performed with 100 µM of BARAC-biotin. The reactions were allowed to proceed for one hour and the labeled protein was analyzed by SDS-PAGE and Western blot. As quantified by ImageJ, reactions mediated by BTTES-Cu(I) and BTTAA-Cu(I) provided 2.6- and 2.1-fold stronger signal than the signal afforded by THPTA-Cu(I) for the fusion protein isolated from $Ac_4ManNAz$-treated culture. By contrast, significantly weaker labeling was observed for the click reaction mediated by THPTA, and no detectable signal was observed for the reactions mediated by TBTA-Cu(I) and BARAC.

Figure 13:
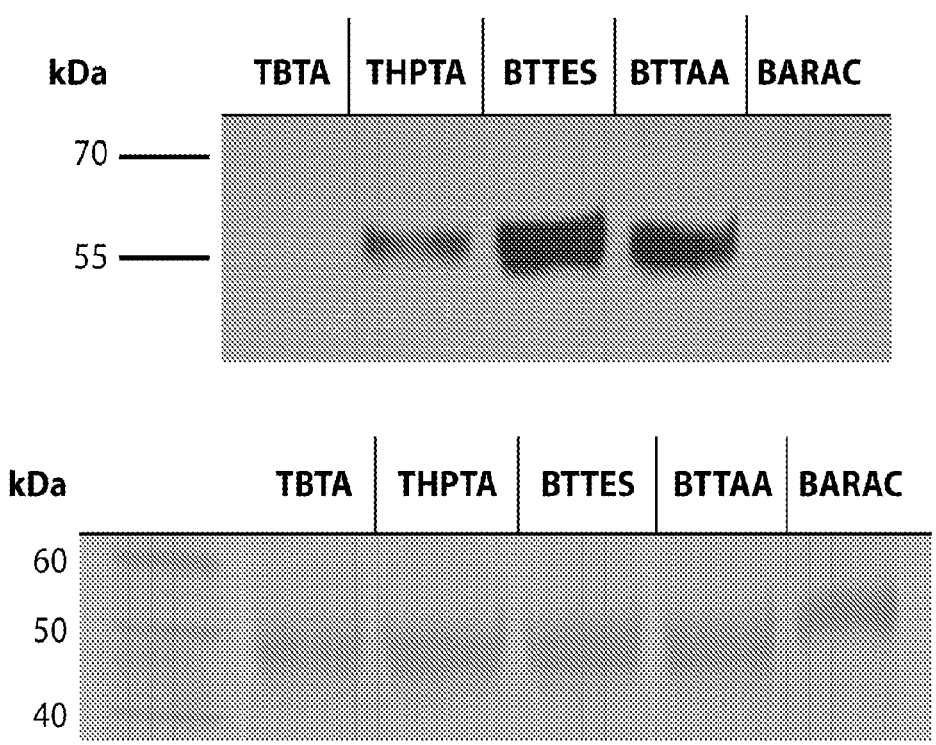
FIG. 13. Comparison of the efficiency of the CuAAC and BARAC-mediated copper-free click chemistry in labeling recombinant proteins and crude cell lysates. Western blot analysis of PD1-Fc isolated from HEK cells treated with Ac$_4$ManNAz (top panel). Total protein loading was confirmed by Coomassie staining (bottom panel). Reaction conditions for CuAAC: biotin-alkyne (100 μM) in the presence of sodium ascorbate (2.5 mM), CuSO$_4$ (250 μM) premixed with various tristriazolylamino ligands (500 μM); copper-free click reaction: BARAC-biotin (100 μM). Reactions were allowed to proceed for 1 h at room temperature, and analyzed by Western blot using an HRP-conjugated anti-biotin antibody. Structural formulae of tris(triazolylmethyl)amine-based ligands and BARAC-biotin. BTTAA=2-[4-({bis[(1-tert-butyl-1H-1,2,3-triazol-4-yl)methyl]amino}methyl)-1H-1,2,3-triazol-1-yl]acetic acid, BTTES=2-[4-({bis[(1-tert-butyl-1H-1,2,3-triazol-4-yl)methyl]amino}methyl)-1H-1,2,3-triazol-1-yl]ethyl hydrogen sulfate, TBTA=tris[(1-benzyl-1H-1,2,3-triazol-4-yl)methyl]amine, THPTA=tris[(1-hydroxypropyl-1H-1,2,3-triazol-4-yl)methyl]amine, BARAC=biarylazacyclooctynone.

Labeling of PD1-Fc Via the CuAAC and Cu Free Click Chemistry and Detection by Western Blot (FIG. 13)

Purified recombinant PD1-Fc metabolically labeled with $Ac_4ManNAz$ was diluted in lysis buffer (100 mM $Na_3PO_4$, 150 mM NaCl, 1% NP-40, pH 7.4) at a concentration of 0.2 mg/mL and reacted with 100 µM biotin-alkyne in a 100 µL reaction containing premixed ligand-$CuSO_4$ complex ([ligand]:[$CuSO_4$]=2:1, [$CuSO_4$]=250 µM) and 2.5 mM freshly prepared sodium ascorbate. Ligands used included BTTAA, BTTES, TBTA and THPTA. For Cu-free click chemistry, 0.2 mg/mL purified protein was reacted with or 100 µM BARAC-biotin in a 100 µL reaction. The samples were lightly vortexed and allowed to react for 1 hour (25° C., 800 rpm in eppendorf Theromomixer R). The samples were resolved on 4-20% Precise™ Protein Gels (Pierce) (6 µg protein/well). The samples were transferred to nitrocellulose, and incubated for 1 hr at room temperature in blocking buffer (5% non-fat milk in 1×TBST (Tris buffered saline with 0.1% Tween-20, pH 7.5)). The blocked membrane was incubated for 1 hour at room temperature with an HRP-anti-biotin antibody (1:100,000 dilution) in blocking buffer, washed with 1×TBST (3×, 15 min/wash) and developed using SuperSignal® West Pico Chemiluminescent Substrate (Pierce). X-OMAT LS film (Kodak) was used to detect the chemiluminescence. Coomassie Blue staining was used to verify equal protein loading.

REFERENCES

1. Kolb, H. C., Finn, M. G. & Sharpless, K. B. Click Chemistry: Diverse Chemical Function from a Few Good Reactions. Angew. Chem. Int. Ed. 40, 2004-2021 (2001).
2. Baskin, J. M. & Bertozzi, C. R. Bioorthogonal click chemistry: Covalent labeling in living systems. Qsar Comb. Sci. 26, 1211-1219 (2007).
3. Wang, L. & Schultz, P. G. Expanding the genetic code. Angew. Chem. Int. Ed. 44, 34-66 (2004).
4. Laughlin, S. T. et al. Metabolic labeling of glycans with azido sugars for visualization and glycoproteomics. Methods Enzymol. 415, 230-250 (2006).
5. Dieterich, D. C. et al. Labeling, detection and identification of newly synthesized proteomes with bioorthogonal non-canonical amino-acid tagging. Nat. Protc. 2, 532-540 (2007).
6. Prescher, J. A. & Bertozzi, C. R. Chemistry in living systems. Nat. Chem. Biol. 1, 13-21 (2005).
7. Sletten, E. M. & Bertozzi, C. R. Bioorthogonal chemistry: fishing for selectivity in a sea of functionality. Angew. Chem. Int. Ed. 48, 6974-6998 (2009).
8. Rostovtsev, V. V., Green, L. G., Fokin, V. V. & Sharpless, K. B. A stepwise huisgen cycloaddition process: copper (I)-catalyzed regioselective "ligation" of azides and terminal alkynes. Angew. Chem. Int. Ed. 41, 2596-2599 (2002).
9. Tomoe, C. W., Christensen, C. & Meldal, M. Peptidotriazoles on solid phase: [1,2,3]-triazoles by regiospecific copper(i)-catalyzed 1,3-dipolar cycloadditions of terminal alkynes to azides. J. Org. Chem. 67, 3057-3064 (2002).
10. Wu, P. & Fokin, V. V. Catalytic azide-alkyne cycloaddition: Reactivity and applications. Aldrich. Acta 40, 7-17 (2007).
11. Chan, T. R., Hilgraf, R., Sharpless, K. B. & Fokin, V. V. Polytriazoles as copper(I)-stabilizing ligands in catalysis. Org. Lett. 6, 2853-2855 (2004).
12. Kolb, H. C. & Sharpless, K. B. The growing impact of click chemistry on drug discovery. Drug Discov. Today 8, 1128-1137 (2003).
13. Lutz, J. F. 1,3-dipolar cycloadditions of azides and alkynes: a universal ligation tool in polymer and materials science. Angew. Chem. Int. Ed. 46, 1018-1025 (2007).
14. Gaetke, L. M. & Chow, C. K. Copper toxicity, oxidative stress, and antioxidant nutrients. Toxicology 189, 147-163 (2003).
15. Link, A. J., Vink, M. K. & Tirrell, D. A. Presentation and detection of azide functionality in bacterial cell surface proteins. J. Am. Chem. Soc. 126, 10598-10602 (2004).
16. Agard, N. J., Prescher, J. A. & Bertozzi, C. R. A strain-promoted [3+2] azide-alkyne cycloaddition for covalent modification of biomolecules in living systems. J. Am. Chem. Soc. 126, 15046-15047 (2004).
17. Jewett, J. C. & Bertozzi, C. R. Cu-free click cycloaddition reactions in chemical biology. Chem. Soc. Rev. 39, 1272-1279.
18. Baskin, J. M. et al. Copper-free click chemistry for dynamic in vivo imaging. Proc. Natl. Acad. Sci. USA 104, 16793-16797 (2007).
19. Jewett, J. C., Sletten, E. M. & Bertozzi, C. R. Rapid Cu-free click chemistry with readily synthesized biarylazacyclooctynones. J. Am. Chem. Soc. 132, 3688-3690 (2010).
20. Laughlin, S. T. & Bertozzi, C. R. In vivo imaging of *Caenorhabditis elegans* glycans. ACS Chem. Biol. 4, 1068-1072 (2009).
21. Laughlin, S. T., Baskin, J. M., Amacher, S. L. & Bertozzi, C. R. In vivo imaging of membrane-associated glycans in developing zebrafish. Science 320, 664-667 (2008).
22. Chang, P. V. et al. Copper-free click chemistry in living animals. Proc. Natl. Acad. Sci. USA 107, 1821-1826 (2010).
23. Poloukhtine, A. A., Mbua, N. E., Wolfert, M. A., Boons, G. J. & Popik, V. V. Selective labeling of living cells by a photo-triggered click reaction. J. Am. Chem. Soc. 131, 15769-15776 (2009).
24. Kaim, W. & Rall, J. Copper—A "modern" bioelement. Angew. Chem. Int. Ed. 35, 43-60 (1996).
25. Solomon, E. I., Tuczek, F., Root, D. E. & Brown, C. A. Spectroscopy of Binuclear Dioxygen Complexes. Chem. Rev. 94, 827-856 (1994).
26. Solomon, E. I., Chen, P., Metz, M., Lee, S. K. & Palmer, A. E. Oxygen binding, activation, and reduction to water by copper proteins. Angew. Chem. Int. Ed. 40, 4570-4590 (2001).
27. Decker, A. & Solomon, E. I. Dioxygen activation by copper, heme and non-heme iron enzymes: comparison of electronic structures and reactivities. Curr. Opin. Chem. Biol. 9, 152-163 (2005).
28. Pierre, J.-L. et al. Imidazolate-bridged dicopper(II) and copper-zinc complexes of a macrobicyclic ligand (cryptand). A possible model for the chemistry of Cu—Zn superoxide dismutase. J. Am. Chem. Soc. 117, 1965-1973 (1995).
29. Mohindru, A., Fisher, J. M. & Rabinovitz, M. Bathocuproine sulphonate: a tissue culturecompatible indicator of copper-mediated toxicity. Nature 303, 64-65 (1983).
30. Marx, M., Rutishauser, U. & Bastmeyer, M. Dual function of polysialic acid during zebrafish central nervous system development. Development 128, 4949-4958 (2001).
31. Bentrop, J., Marx, M., Schattschneider, S., Rivera-Milla, E. & Bastmeyer, M. Molecular evolution and expression of zebrafish St8SiaIII, an alpha-2,8-sialyltransferase involved in myotome development. Dev. Dyn. 237, 808-818 (2008).
32. Harduin-Lepers, A. et al. Evolutionary history of the alpha2,8-sialyltransferase (ST8Sia) gene family: tandem duplications in early deuterostomes explain most of the diversity found in the vertebrate ST8Sia genes. BMC Evol. Biol. 8, 258 (2008).
33. Chang, L. Y. et al. Molecular cloning and characterization of the expression pattern of the zebrafish alpha2, 8-sialyltransferases (ST8Sia) in the developing nervous system. Glycoconj. J. 26, 263-275 (2009).
34. Becker, D. J. & Lowe, J. B. Fucose: biosynthesis and biological function in mammals. Glycobiology 13, 41R-53R (2003).
35. Saito, S., Liu, B. & Yokoyama, K. Animal embryonic stem (ES) cells: self-renewal, pluripotency, transgenesis and nuclear transfer. Hum. Cell 17, 107-115 (2004).
36. Ohata, S. et al. Neuroepithelial cells require fucosylated glycans to guide the migration of vagus motor neuron progenitors in the developing zebrafish hindbrain. Development 136, 1653-1663 (2009).
37. Hsu, T. L. et al. Alkynyl sugar analogs for the labeling and visualization of glycoconjugates in cells. Proc. Natl. Acad. Sci. USA 104, 2614-2619 (2007).
38. Sawa, M. et al. Glycoproteomic probes for fluorescent imaging of fucosylated glycans in vivo. Proc. Natl. Acad. Sci. USA 103, 12371-12376 (2006).
39. Wang, W. et al. Chemoenzymatic synthesis of GDP-L-fucose and the Lewis X glycan derivatives. Proc. Natl. Acad. Sci. USA 106, 16096-16101 (2009).
40. Ma, B., Simala-Grant, J. L. & Taylor, D. E. Fucosylation in prokaryotes and eukaryotes. Glycobiology 16, 158R-184R (2006).
41. Guerardel, Y., Chang, L. Y., Maes, E., Huang, C. J. & Khoo, K. H. Glycomic survey mapping of zebrafish identifies unique sialylation pattern. Glycobiology 16, 244-257 (2006).
42. Laughlin, S. T. & Bertozzi, C. R. Imaging the glycome. Proc. Natl. Acad. Sci. USA 106, 12-17 (2009).
43. White, R. M. et al. Transparent adult zebrafish as a tool for in vivo transplantation analysis. Cell Stem Cell 2, 183-189 (2008).
44. Lister, J. A., Robertson, C. P., Lepage, T., Johnson, S. L. & Raible, D. W. nacre encodes a zebrafish microphthalmia-related protein that regulates neural-crest-derived pigment cell fate. Development 126, 3757-3767 (1999).
45. Laughlin, S. T. et al. Metabolic labeling of glycans with azido sugars for visualization and glycoproteomics. Methods Enzymol. 415, 230-250 (2006).
46. Chang, P. V. et al. Metabolic labeling of sialic acids in living animals with alkynyl sugars. Angew. Chem. Int. Ed. 48, 4030-4033 (2009).

47. Yu, H., Yu, H., Karpel, R. & Chen, X. Chemoenzymatic synthesis of CMP-sialic acid derivatives by a one-pot two-enzyme system: comparison of substrate flexibility of three microbial CMP-sialic acid synthetases. Bioorg. Med. Chem. 12, 6427-6435 (2004).
48. Wang, W. et al. Chemoenzymatic synthesis of GDP-L-fucose and the Lewis X glycan derivatives. Proc. Natl. Acad. Sci. USA 106, 16096-16101 (2009).
49. Hang, H. C., Yu, C., Pratt, M. R. & Bertozzi, C. R. Probing glycosyltransferase activities with the Staudinger ligation. J Am Chem Soc 126, 6-7 (2004).
50. Agard, N. J., Prescher, J. A. & Bertozzi, C. R. A strain-promoted [3+2] azide-alkyne cycloaddition for covalent modification of biomolecules in living systems. J. Am. Chem. Soc. 126, 15046-7 (2004).
51. Bottaro, J. C., Penwell, P. E. & Schmitt, R. J. Expedient synthesis of t-butyl azide. Synthetic Comm. 27, 1465-1467 (1997).
52. Hong, V., Presolski, S. I., Ma, C. & Finn, M. G. Analysis and optimization of copper-catalyzed azide-alkyne cycloaddition for bioconjugation. Angew. Chem. Int. Ed. 48, 9879-83 (2009).

What is claimed is:

1. A composition comprising a ligand for use in an azide-alkyne cycloaddition reaction and $CuSO_4$, wherein the ligand is in complex with $CuSO_4$ in a ratio of ligand:$CuSO_4$ of at least 2:1 and wherein the ligand comprises a tris(triazolylmethyl)amine of formula (I):

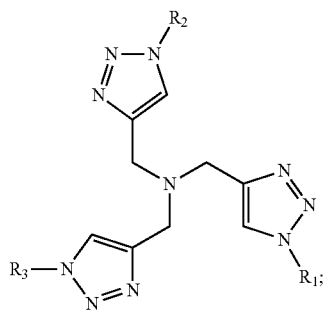
(I)

wherein R1 and R2 are

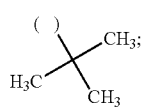

wherein R3 is

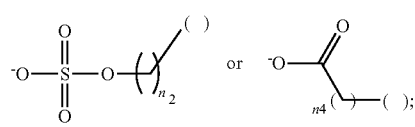

wherein n2 is 2-3, and n4 is 1-2; and wherein ( ) is the point of attachment of the R1, R2, or R3 group to the ring structure.

2. The composition of claim 1, wherein the ligand comprises

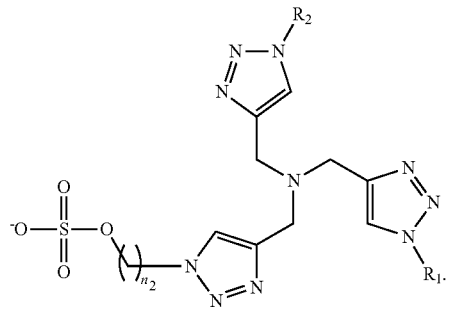

3. The composition of claim 1, wherein the ligand comprises

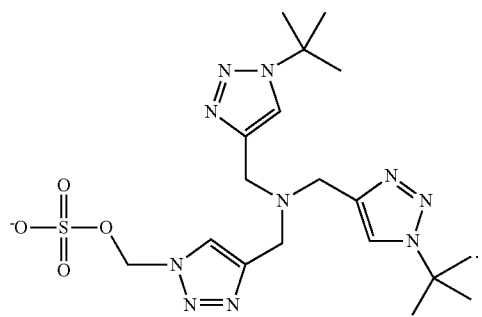

4. The composition of claim 1, wherein the ligand comprises

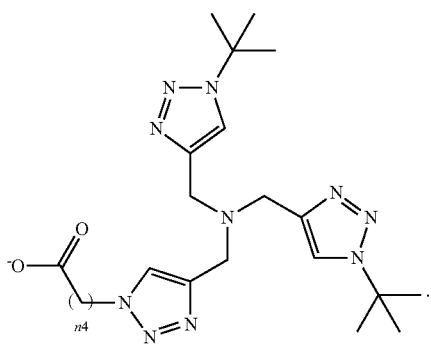

5. The composition of claim 1, wherein the wherein the ligand is in complex with $CuSO_4$ in a ratio of ligand:$CuSO_4$ of 2:1 to 7:1.

6. The composition of claim 1, wherein the wherein the ligand is in complex with $CuSO_4$ in a ratio of ligand:$CuSO_4$ of 5:1 to 6:1.

7. The composition of claim 1, wherein the wherein the ligand is in complex with $CuSO_4$ in a ratio of ligand:$CuSO_4$ of 6:1.

8. A compound selected from the group consisting of
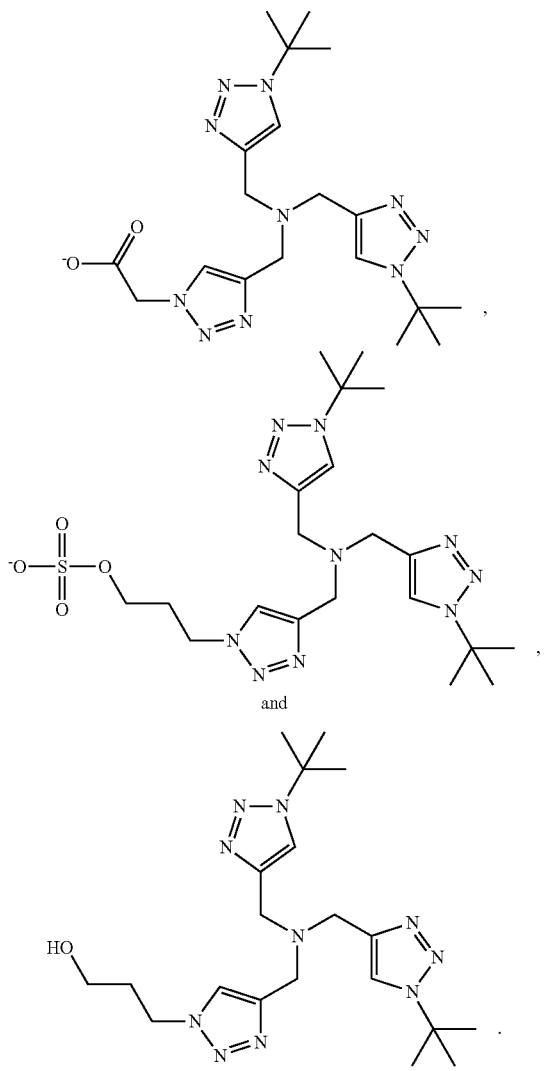
and
9. A compound having the structure of formula (I):
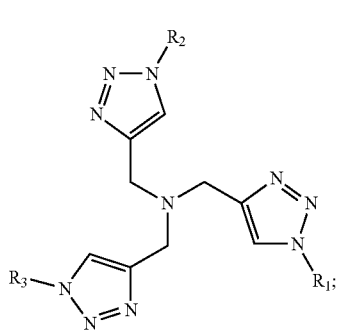
wherein R1 and R2 are
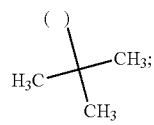
wherein R3 is
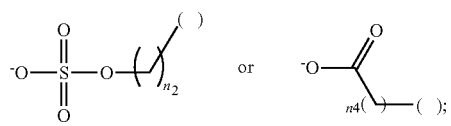
wherein n2 is 2-3, and n4 is 1-2; and wherein ( ) is the point of attachment of the R1, R2, or R3 group to the ring structure.
* * * * *